United States Patent
Quinn et al.

(10) Patent No.: US 9,034,006 B2
(45) Date of Patent: May 19, 2015

(54) METHOD AND APPARATUS FOR RETRIEVING AN EMBOLIZED IMPLANT

(75) Inventors: Chris Quinn, Minneapolis, MN (US); Steve Zaver, Plymouth, MN (US); Kevin Anderson, Brooklyn Center, MN (US)

(73) Assignee: ATRITECH, INC., Plymouth, MN (US)

(*) Notice: Subject to any disclaimer, the term of this patent is extended or adjusted under 35 U.S.C. 154(b) by 1721 days.

(21) Appl. No.: 11/607,638

(22) Filed: Dec. 1, 2006

(65) Prior Publication Data

US 2007/0162048 A1 Jul. 12, 2007

Related U.S. Application Data

(60) Provisional application No. 60/741,262, filed on Dec. 1, 2005.

(51) Int. Cl.
| | |
|---|---|
| *A61M 29/00* | (2006.01) |
| *A61B 17/221* | (2006.01) |
| *A61B 17/12* | (2006.01) |
| *A61B 17/3205* | (2006.01) |
| *A61B 17/22* | (2006.01) |

(52) U.S. Cl.
CPC ......... *A61B 17/221* (2013.01); *A61B 17/12022* (2013.01); *A61B 17/12122* (2013.01); *A61B 17/12172* (2013.01); *A61B 17/32056* (2013.01); *A61B 2017/22035* (2013.01); *A61B 2017/12054* (2013.01)

(58) Field of Classification Search
USPC ......... 606/106, 108, 113, 114, 157, 194, 195, 606/200; 623/1.11; 128/898, 899
See application file for complete search history.

(56) References Cited

U.S. PATENT DOCUMENTS

| | | | | |
|---|---|---|---|---|
| 4,969,891 | A | * | 11/1990 | Gewertz .................. 606/200 |
| 5,098,440 | A | * | 3/1992 | Hillstead ................. 606/108 |
| 5,211,658 | A | | 5/1993 | Clouse |
| 5,300,086 | A | * | 4/1994 | Gory et al. ............... 606/200 |
| 5,370,657 | A | * | 12/1994 | Irie ........................ 606/200 |
| 5,464,408 | A | | 11/1995 | Duc |
| 5,634,942 | A | | 6/1997 | Chevillon et al. |
| 5,643,282 | A | | 7/1997 | Kieturakis |
| 5,709,704 | A | | 1/1998 | Nott et al. |
| 5,733,302 | A | | 3/1998 | Myler et al. |
| 5,746,767 | A | | 5/1998 | Smith |
| 6,152,144 | A | | 11/2000 | Lesh et al. |
| 6,156,055 | A | | 12/2000 | Ravenscroft |
| 6,214,029 | B1 | | 4/2001 | Thill et al. |
| 6,371,971 | B1 | | 4/2002 | Tsugita et al. |
| 6,440,152 | B1 | | 8/2002 | Gainor et al. |
| 6,447,530 | B1 | | 9/2002 | Ostrovsky et al. |

(Continued)

OTHER PUBLICATIONS http://dictionary.reference.com/browse/embolize, dictionary definition of the term "embolized" retrieved Jan. 9, 2012.*

(Continued)

*Primary Examiner* — David Eastwood
(74) *Attorney, Agent, or Firm* — Seager, Tufte & Wickhem LLC

(57) ABSTRACT

A retrieval portion is attached to an implantable device to facilitate retrieval of the implantable device in the unlikely event of embolization. The retrieval portion may comprise one or more loops, or a plurality of extensions. Methods of retrieving an implantable device are disclosed. Various adapters are disclosed for use with a conventional snare for grasping an implantable device.

4 Claims, 26 Drawing Sheets

(56) References Cited

U.S. PATENT DOCUMENTS

| | | | |
|---|---|---|---|
| 6,551,303 | B1 | 4/2003 | Van Tassel et al. |
| 6,837,901 | B2 | 1/2005 | Rabkin et al. |
| 7,044,134 | B2 | 5/2006 | Khairkhahan et al. |
| 2002/0035374 | A1* | 3/2002 | Borillo et al. .................. 606/194 |
| 2003/0195555 | A1* | 10/2003 | Khairkhahan et al. ......... 606/200 |
| 2004/0133230 | A1* | 7/2004 | Carpenter et al. ............. 606/191 |
| 2004/0138693 | A1* | 7/2004 | Eskuri et al. ................... 606/200 |
| 2004/0181237 | A1* | 9/2004 | Forde et al. .................... 606/108 |
| 2004/0267306 | A1 | 12/2004 | Blaeser et al. |
| 2005/0038470 | A1 | 2/2005 | van der Burg et al. |
| 2006/0241675 | A1 | 10/2006 | Johnson et al. |

OTHER PUBLICATIONS http://dictionary.reference.com/browse/embolus, dictionary definition of the term "embolus" retrieved Jan. 9, 2012.*
http://dictionary.reference.com/browse/loop, dictionary definition of the term "loop" retrieved Jan. 9, 2012.*

* cited by examiner

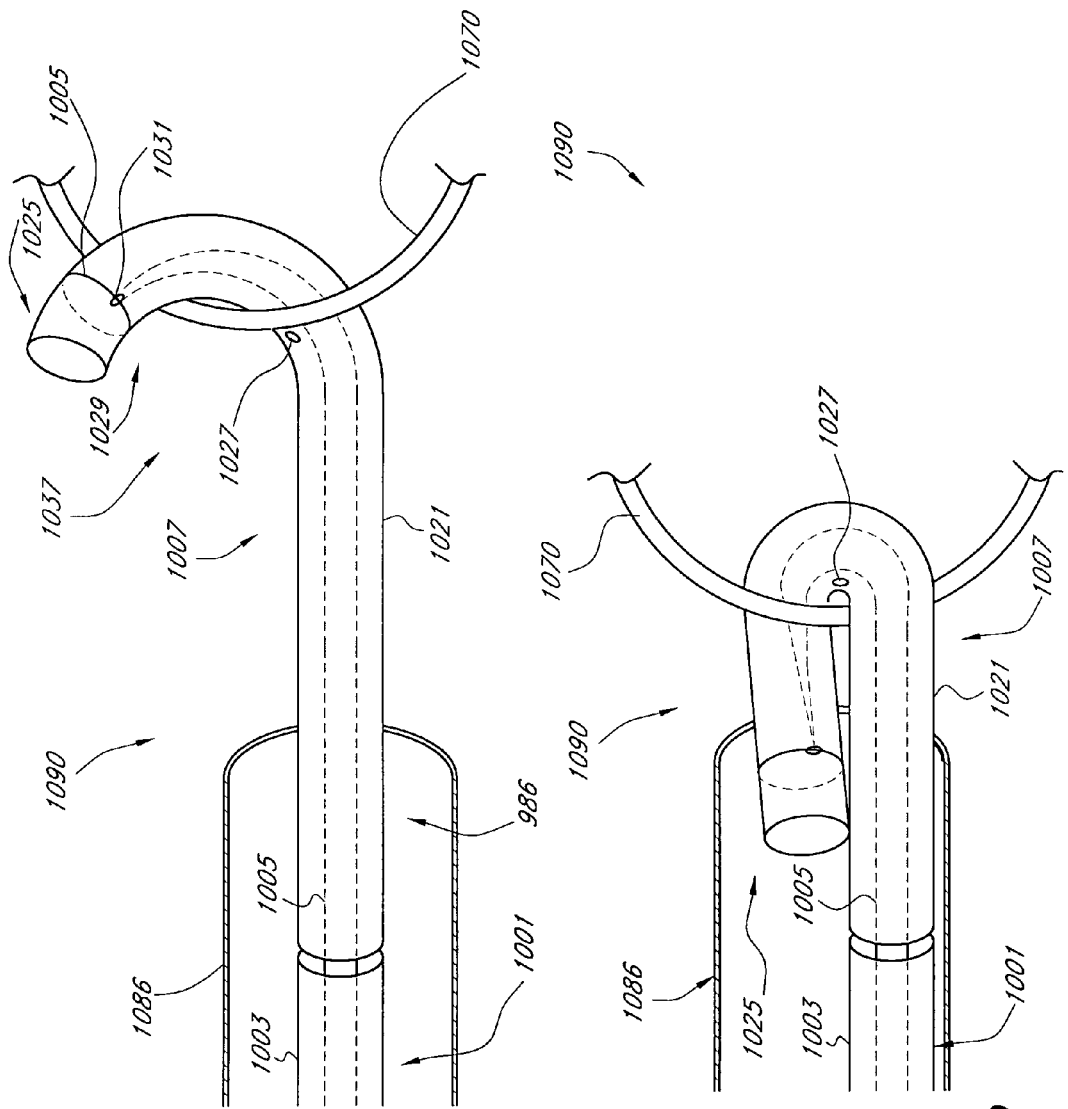

METHOD AND APPARATUS FOR RETRIEVING AN EMBOLIZED IMPLANT

CROSS-REFERENCE TO RELATED APPLICATIONS

This application claims the benefit of U.S. provisional application No. 60/741262, filed Dec. 1, 2005, the entirety of which is hereby incorporated by reference.

BACKGROUND OF THE INVENTION

1. Field of the Invention

Embodiments of the present invention relate to implantable devices and systems, devices and methods for their retrieval from the body, particularly devices that embolize during attempts to deliver the device to a left atrial appendage.

2. Description of the Related Art

There are a multitude of medical devices suitable for implantation within a lumen or organ of the human body. For example, it is well known that a variety of stents and stent-like devices are suitable for implantation within the vasculature or any other bodily lumen or structure, such as blood vessels, including arteries, veins, and the heart. In some situations it is desired to provide an implantable device inside of the left atrial appendage (LAA) of the heart. Embodiments of such a device are described in U.S. application Ser. No. 10/642,384, filed Aug. 15, 2003, published as US 2005/0038470 A1, which is incorporated by reference herein.

If an implantable device becomes dislodged from the site to which it was delivered it may be carried by bodily fluids from the delivery site. When this occurs, the device may be described as having embolized. As the device is carried away it may rotate or otherwise change its spatial orientation. It would be advantageous to be able to percutaneously retrieve such implantable devices from the body.

SUMMARY OF THE INVENTION

In one embodiment, a retrieval portion is attached to an implantable device to facilitate retrieval of the implantable device in the unlikely event of embolization. The retrieval portion may comprise one or more loops, or a plurality of extensions. Methods of retrieving an implantable device are disclosed. The implantable device may be retrieved after release from the left atrial appendage. Various adapters are disclosed for use with a conventional snare for grasping an implantable device.

In one embodiment, an apparatus is provided for facilitating removal of an implantable device from an opening within a patient. The apparatus may comprise a support structure having a proximal end and a distal end, the support structure being expandable to an enlarged configuration and collapsible to a reduced configuration, and a retrieval portion extending distally from the distal end of the support structure. The retrieval portion may comprise at least one loop.

In another embodiment, an apparatus is provided for facilitating removal of an implantable device for a left atrial appendage of a patient. The apparatus may comprise a support structure comprising means for containing particles within the left atrial appendage and means provided on the support structure for retrieving the support structure from the patient in the event that the support structure embolizes.

In one embodiment, a method is provided for removing an embolized implant from a patient, wherein the embolized implant is released from the left atrial appendage. The method may comprise positioning a sheath near the embolized implant; inserting a retrieval device through the sheath; coupling the retrieval device to a retrieval portion of the embolized implant, the retrieval portion extending from the distal end of the implant; and retracting the embolized implant into the sheath.

All of these embodiments are intended to be within the scope of the present invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 31 is a schematic partial cross-sectional view of a retrieval device in accordance with another embodiment.

FIG. 32 is a schematic partial cross-sectional view as in FIG. 31, showing the retrieval device partially retracted into a sheath.

DETAILED DESCRIPTION OF CERTAIN PREFERRED EMBODIMENTS

Embodiments of the present invention related to methods and apparatuses for retrieval of implantable devices from the anatomy. One such implantable device and system is known to those of skill in the art as the PLAATO™ system from ev3 Inc. Although preferred embodiments are described with respect to LAA implants, it will be appreciated that embodiments as described herein may be applied to any suitable device, such as for delivering or implanting into other bodily locations or openings. Similar references numerals will be used to designate similar components in the different embodiments. Additionally, some embodiments can include one or more features described in connection with one or more of the embodiments described herein.

Figure 1:
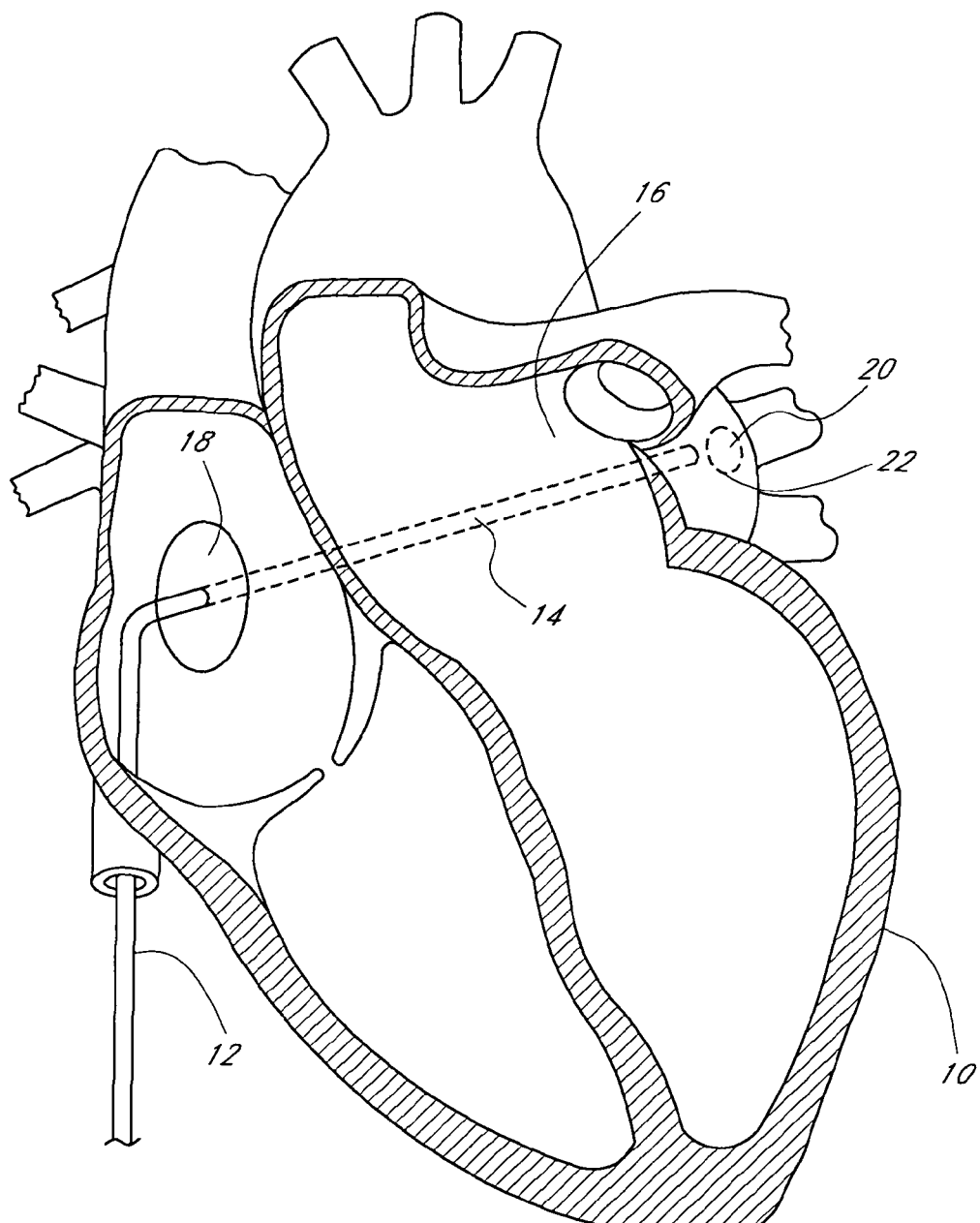
FIG. 1 is a schematic view of a patient's heart with a transseptal sheath deployed through the septum.
Figure 2:
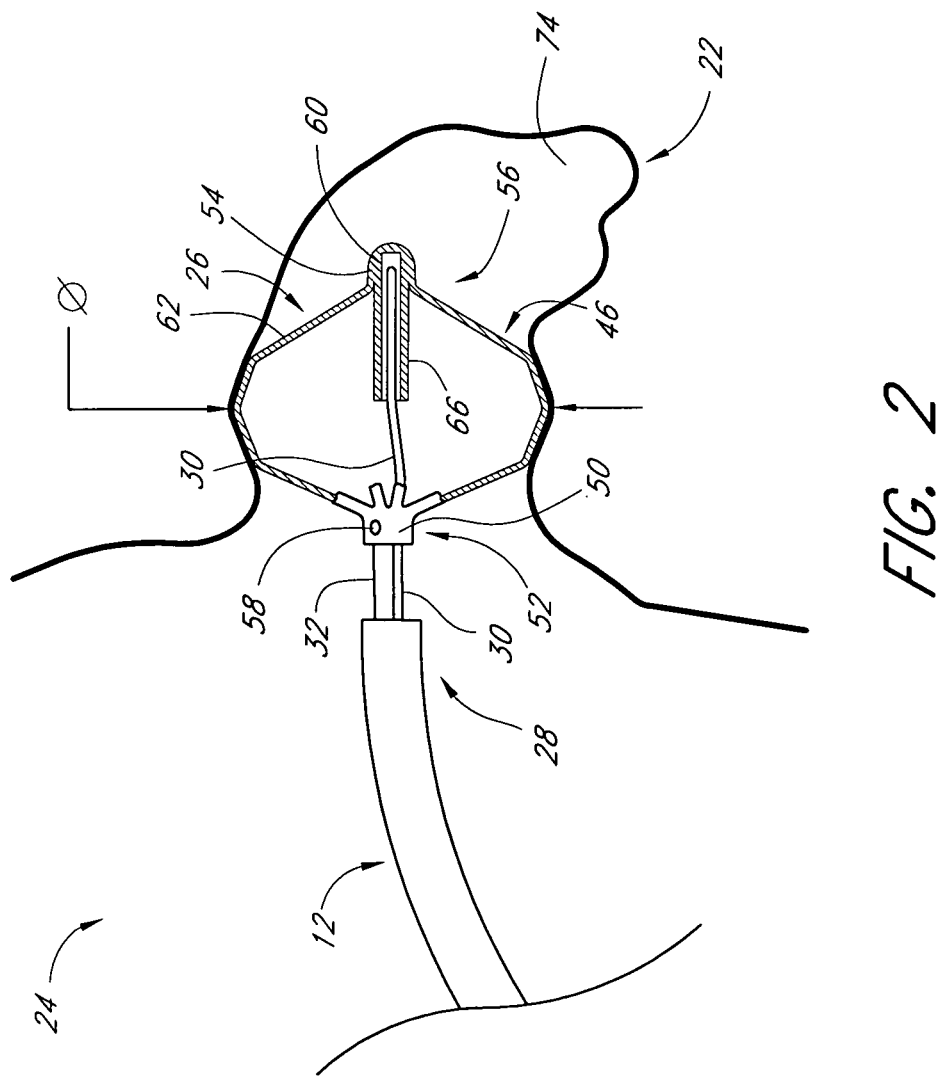
FIG. 2 is a schematic view of a deployment system delivering an implant to the left atrial appendage.

Referring to FIG. 1, a schematic view of a patient's heart 10 in partial section shows a transseptal sheath 12 having a distal end 14. The distal end 14 of the transseptal sheath 12 has breached the septum 18 of the patient's heart 10 and is disposed within the left atrium 16 adjacent the opening 20 of the patient's left atrial appendage 22 (LAA 22). FIG. 2 illustrates a deployment system 24, having an implant 26 and a delivery system 28. The implant 26 may be designed to occlude or contain particles within the LAA 22 and prevent thrombus from forming in, and emboli from originating from, the LAA 22 in a patient with atrial fibrillation. The delivery system 28 preferably is compatible for use with the transseptal sheath 12. The delivery system preferably comprises an axially movable core 30 and a control wire 32. The delivery system 28 and implant 26 preferably are designed to allow the implant 26 to be positioned, repositioned, and retrieved from the LAA 22 if necessary.

Figure 4:
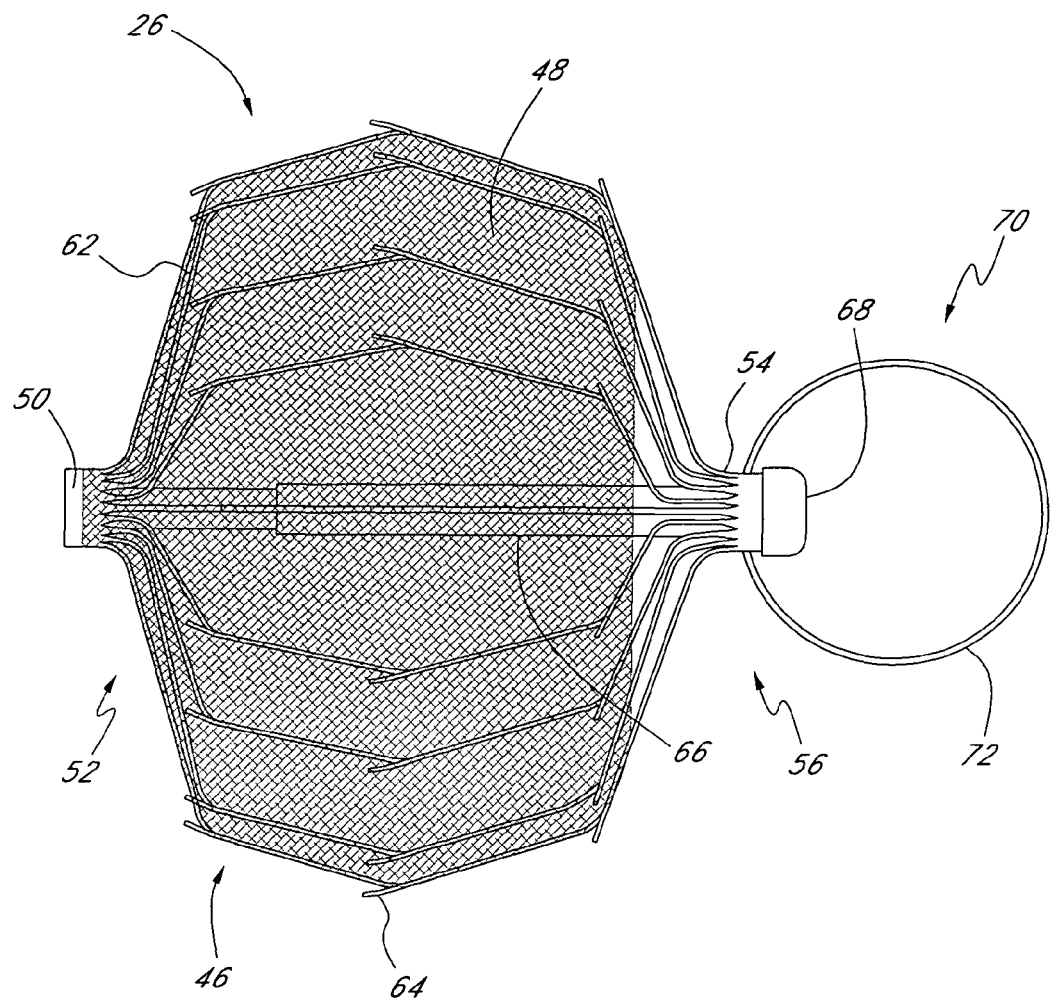
FIG. 4 is a plan view of a LAA implant with a retrievable portion in accordance with one embodiment.

The implant 26 preferably comprises a frame 46 and a membrane 48 (shown in FIG. 4). The implant 26 when expanded preferably extends from a proximal hub 50 at a proximal end 52 increasing in diameter to an apex or apex portion, then decreasing to a distal hub 54 at a distal end 56. In some embodiments, the proximal hub 50 is coupled with a proximal crosspin 58. The distal hub 54 preferably is coupled with a plug or cap 60.

A plurality of supports 62 extend between a proximal hub 50 and a distal hub 54. In one embodiment, sixteen supports 62 are provided. However, the precise number of supports 62 can be modified, depending upon the desired physical properties of the implant 26 as will be apparent to those of skill in the art in view of the disclosure herein, without departing from the present invention.

Preferably, the supports 62 comprise a metal such as stainless steel, nitinol, Elgiloy, or others which can be determined through routine experimentation by those of skill in the art. The frame 46 preferably is constructed of self-expanding nitinol supports. Wires having a circular or rectangular cross-section may be utilized depending upon the manufacturing technique. In one embodiment, rectangular cross section supports are cut such as by known laser cutting techniques from tube stock, a portion of which forms the hubs 50 and 54.

The implant 26 preferably comprises anchors 64 that extend from the frame 46 when the implant 26 is expanded. At least some of the supports 62, and, preferably, each support 62, is provided with one or two or more barbs 64. In one embodiment, each support 62 has three barbs 64. As illustrated in FIG. 4, the implant 26 is in its enlarged orientation, such as for occluding a left atrial appendage or other body cavity or lumen. In this orientation, each of the barbs 46 projects generally radially outwardly from the implant 26, and is inclined in the proximal direction. This is to inhibit proximal migration of the implant out of the left atrial appendage. One or more barbs may also be inclined distally. In this context, distal refers to the direction into the left atrial appendage, and proximal refers to the direction from the left atrial appendage into the heart. In an embodiment where the barbs 64 and corresponding support 62 are cut from a single ribbon, sheet or tube stock, the barb 64 will incline radially outwardly at approximately a tangent to the curve formed by the support 46.

In the illustrated embodiment, the distal end 56 of the implant 26 is provided with a plug or cap 60. In one embodiment, the plug 60 comprises an atraumatic tip, such that contact between the atraumatic tip and the inside surface of the LAA 22 does not cause significant damage to the LAA 22.

Various distal end 56 constructions may be utilized, as will be apparent to those of skill in the art in view of the disclosure herein. In the embodiment illustrated in FIG. 2, the plug 60 may be attached to a distal end of a distal guide tube 66, described in greater detail below. The plug 60 may be secured to the guide tube 66 and implant 26 in any of a variety of ways, depending upon the various construction materials. For example, any of a variety of metal bonding techniques such as a welding, brazing, interference fit such as threaded fit or snap fit, may be utilized. Alternatively, any of a variety of bonding techniques for dissimilar materials may be utilized, such as adhesives, and various molding techniques. In one construction, the plug 60 is composed of PEBAX.

The membrane 48, as shown in FIG. 4, preferably is constructed of a fabric covering, such as one made of ePTFE, or an ePTFE/PE laminate. To attach the membrane to the frame 46, a PE mesh preferably is placed against the supports 62, with one sheet of ePTFE preferably placed over the PE mesh and another sheet of ePTFE preferably placed on an opposite side of the supports 62. The membrane 48 preferably is heated on both sides causing the PE to melt into both sheets of ePTFE, thereby surrounding a portion of the frame 46. The nitinol supports allow the implant 26 to self-expand in the appendage 22, covering the orifice with the laminated fabric. The porous ePTFE/PE lamination facilitates rapid endothelialization and healing. The membrane 48 preferably covers at least a proximal face of the device.

The core 30 may comprise any of a variety of structures which has sufficient lateral flexibility to permit navigation of the vascular system, and sufficient axial column strength to enable reduction of the implant 26 to its reduced crossing profile. Any of a variety of structures such as hypotube, solid core wire, "bottomed out" coil spring structures, or combinations thereof may be used, depending upon the desired performance of the finished device. In one embodiment, the core 30 comprises stainless steel tubing.

Referring to FIG. 2, the distal guide tube 66 extends proximally from the distal hub 54. The guide tube 66 receives the distal end of core 30 within a recess or lumen defined by the guide tube 66. Following positioning at or about the desired deployment site, proximal retraction of the core 30 enables the implant 26 to radially enlarge under its own bias to fit the surrounding tissue structure. The guide tube 66 may be a section of tubing such as metal hypotube, which is attached at the distal end 56 of the implant and extends proximally within the implant 26. The guide tube 66 preferably extends a sufficient distance in the proximal direction to inhibit buckling or prolapse of the core 30 when distal pressure is applied to the core to reduce the profile of the implant 26. However, the guide tube 66 should not extend proximally a sufficient distance to interfere with the opening of the implant 26.

As will be appreciated by reference to FIG. 2, the guide tube 66 may operate as a limit on distal axial advancement of the proximal end 50 of implant 26. Thus, the guide tube 66 preferably does not extend sufficiently far proximally from the distal end 56 to interfere with optimal opening of the implant 26. The specific dimensions are therefore relative, and will be optimized to suit a particular intended application. In one embodiment, the implant 26 has an implanted outside diameter within the range of from about 5 mm to about 45 mm, and an axial implanted length within the range of from about 5 mm to about 45 mm. The guide tube 66 may have an overall length of about 3 mm to about 35 mm, and an outside diameter of about 0.095 inches.

The implant 26 is shown expanded within LAA 22 in FIG. 2. The implant 26 preferably meets the following acceptance criteria, associated with the assessment techniques listed below, prior to being released. The assessment techniques to be evaluated preferably include 1) residual compression; 2) implant location; 3) anchor engagement; 4) seal quality; and 5) stability. For residual compression, the implant diameter Ø, as measured by fluoroscopic imaging, preferably is less than the maximum expanded diameter of the implant 26. For implant location, the proximal sealing surface of the implant 26 preferably is positioned between the LAA 22 ostium and sources of thrombus formation (pectinates, secondary lobes, etc.) (preferably imaged in at least two views). For anchor engagement, the implant frame 46 preferably is positioned within the LAA 22 so as to completely engage a middle row of anchors 64 in an LAA 22 wall (preferably imaged in at least two views). For seal quality, the contrast injections preferably show leakage rated no worse than mild (preferably defined as a flow of contrast media, well defined, and filling one-third of the LAA 22 during a proximal injection over a period of up to about five ventricular beats, preferably imaged in at least two views). For stability, there preferably is no migration or movement of the implant 26 relative to the LAA 22 wall as the delivery system 28 is alternately retracted and advanced about 5-10 mm. The stability of the implant 26 preferably is verified in several views using fluoroscopy and echocardiography.

If the implant's position and function are acceptable, and implant recapture is not necessary, the implant 26 preferably is released from the delivery system 28 by decoupling, under fluoroscopy, the axially movable core 30 and control line 32 from the implant 26. Further details regarding LAA devices and related methods are disclosed in U.S. Pat. No. 6,152,144, filed Nov. 6, 1998; U.S. Pat. No. 7,128,073, filed Nov. 8, 1999; U.S. Pat. No. 7,044,134, filed Oct. 19, 2001; and U.S. patent application Ser. No. 10/642,384, filed Aug. 15, 2003 and published as U.S. Pat. Pub. No. 2005/0038470. The entirety of each of these is hereby incorporated by reference.

Figure 3:
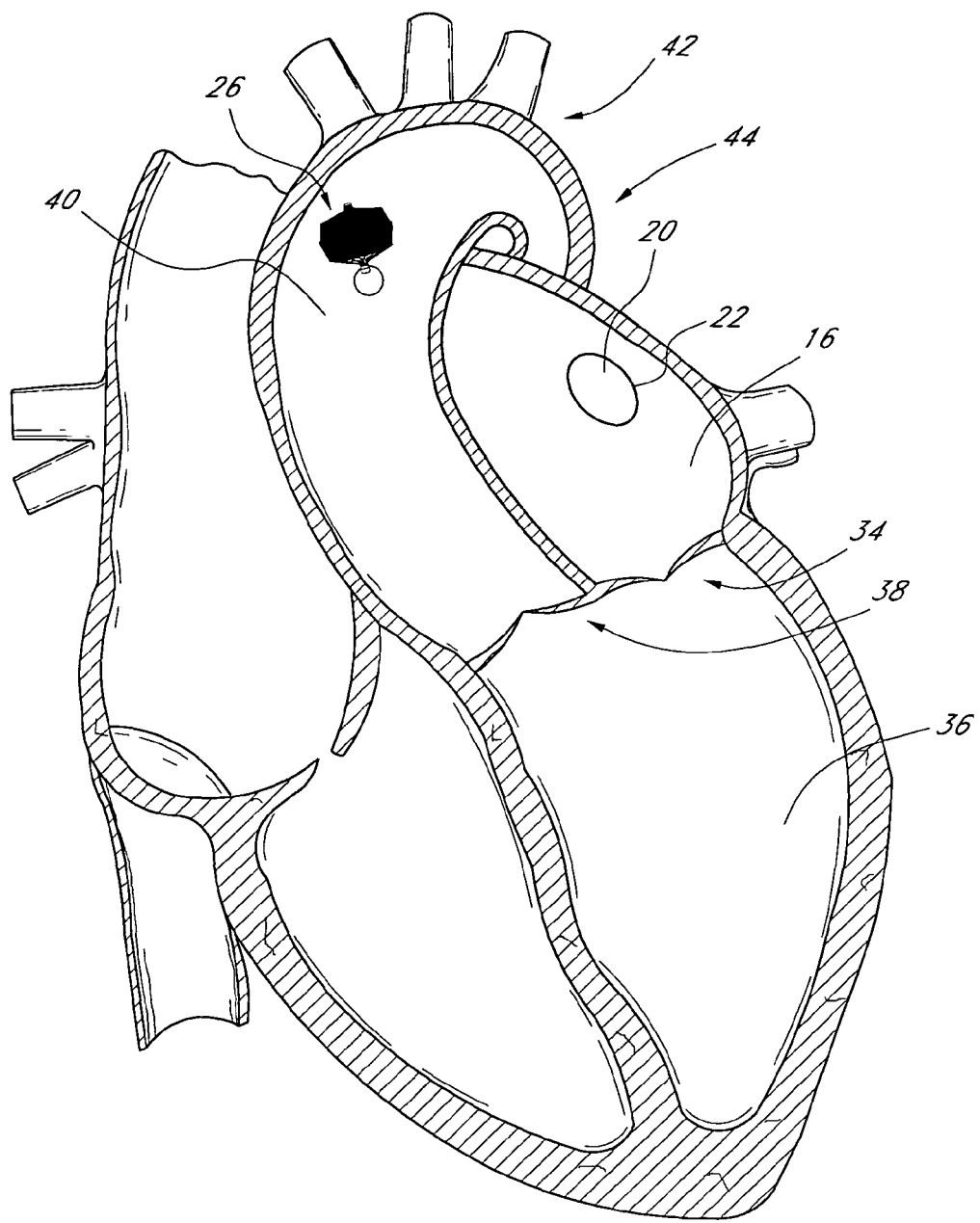
FIG. 3 is a schematic view of a patient's heart with an embolized implant located in the aorta.

In the unlikely event that the device is released without meeting the criteria described above, embolization of the implantable device 26 may occur. Referring to FIG. 3, if the implantable device 26 embolizes, it may be carried by the blood flow from the left atrium 16 through the mitral valve 34 and into the left ventricle 36. From the left ventricle 36 the implant 26 can then be carried through the aortic valve 38 and into the aorta 40. The implant may become lodged in the aortic arch 42 or the descending aorta 44. The implant may also lodge at other locations.

To retrieve the embolized implant 26 it may be desirable to draw the device through the anatomical structures into a sheath (e.g., an outer sheath, transseptal sheath, or a delivery sheath) in such a manner that anchors 64 protruding from the implant 26 do not snag, catch, rip, pinch, pierce, cut and/or otherwise affect the inside wall of the anatomical structure. While certain embodiments are described with reference to an implant for occlusion of a LAA, in other embodiments the implant may be a stent, a cage, a filter, a coil, a clip, or any other implantable support structure. A retrieval portion is connected to the implant to facilitate capture of the implant and allow the device to be pulled proximally into a retrieval sheath for removal from the body. It will be appreciated that retrieval portions may be incorporated with any of the implants described herein, including implants in the patents and applications incorporated by reference. The retrieval portion may be any device that can be coupled to a retrieval catheter to retrieve the implantable device.

The retrieval portion preferably is located in a position that has no negative interactions with the implant anchoring and sealing structures and which presents no additional device handling complexity for the device user. This will reduce regulatory approval needs for the implantable device, potentially avoiding a need for requalification with respect to safety and efficacy. The retrieval portion preferably does not affect expansion or collapse of the implant. One suitable location is distal to the anchoring and sealing structures, where the retrieval portion neither affects the method of implant delivery, expansion, nor collapse.

Figure 5:
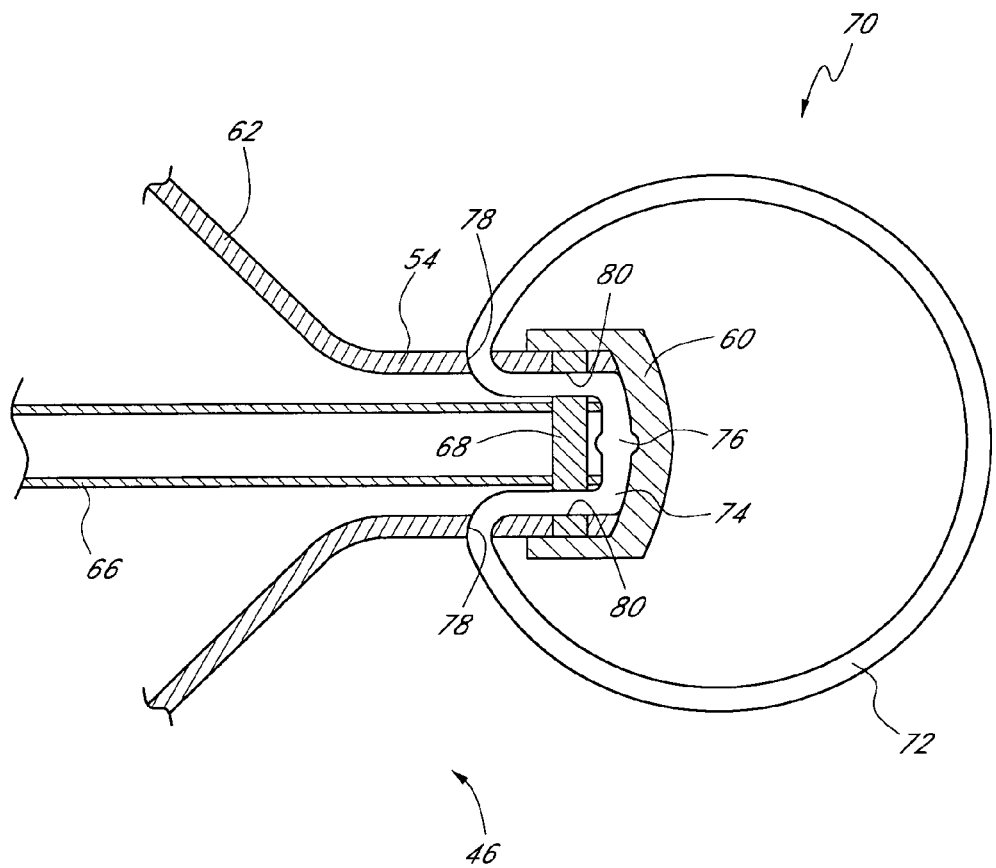
FIG. 5 is an enlarged partial cross-sectional view of the distal end of the implant with the retrievable portion of FIG. 4.

In accordance with one embodiment, illustrated in FIGS. 4 and 5, a retrieval portion 70 is connected to the implant 26. The implant 26 may comprise a frame 46 and a membrane 48. The frame 46 may comprise a proximal hub 50 at a proximal end 52, a distal hub 54 at a distal end 56, and a plurality of supports 62 extending between the proximal hub 50 and the distal hub 54. A plurality of anchors 64 may extend radially and proximally from the supports 62. A distal guide tube 66 may be connected to the frame 46 at the distal end 56 and preferably extends in a proximal direction. The distal guide tube 66 may be connected to the frame 46 by a pin 68, a cap 60, or both.

The retrieval portion 70 may be connected to the implant 26 at the distal end 56, a proximal end 52, or both. In one embodiment, the retrieval portion 70 may be positioned distal to the anchors 64 on the implant 26. The retrieval portion 70 may comprise a loop 72. The loop 72 may be generally circular and may range in diameter from about 2 mm or less to about 25 mm or more. In one embodiment the loop 72 is 7.5 mm in diameter. The loop 72 may be about 0.3 mm or less to about 1 mm or more thick. In one embodiment, the loop 72 is 0.5 mm thick. In one embodiment, the loop is comprised of NITINOL stranded wire having 7 helically wound strands each with a strand diameter of 0.0013", the stranded wire running through the center of a gold coiled wire having a wire diameter of 0.001" and a coil outside diameter of 0.006". The loop 72 may extend distally from the distal hub 54. The loop 72 may be enclosed within the LAA occlusion volume 74 (shown in FIG. 2) when implant 26 is expanded within LAA 22 and should, therefore, not adversely affect the criteria for proper placement described above.

In one embodiment, the loop 72 may be connected to the implant 26 by a segment 74 of loop 72, as shown in FIG. 5. The distal hub 54 may have passages 78. The passages 78 may be holes and may be located proximal to the cap 68. The pin 68 may have passages 80. The loop segment 74 may extend through the passages 78 in the distal hub 54 and the passages 80 in pin 68, between the hub 54 and the distal guide tube 66, and around the end of distal guide tube 66. In this fashion, rotational and translational movement of the loop 72 relative to the implant 226 is restricted to maintain the spacing of the loop 72 from the implant 26.

The retrieval portion 70 preferably is light and flexible, and atraumatic with respect to the inside wall of the cavity, vessel and/or organ into which it is provided. In addition, the retrieval portion 70 preferably is able to withstand strong tension forces provided during implant retrieval. The retrieval portion 70 of the implantable device preferably is compliant so it does not affect implant fit with the cavity, organ or lumen (e.g., the left atrial appendage) into which it is delivered and so that it may be collapsed into a delivery catheter or sheath. The retrieval portion 70 may be made from any material suitable for implantation within the body. For example, the retrieval portion can be made from metal, stainless steel, gold, platinum, tungsten, other radiopaque alloys, plastic, string, NYLON, a combination of such materials, or any other suitable material in monofilament, stranded, or cabled forms. In one embodiment, the retrieval loop may be self-expanding and made from stranded NITINOL (e.g., a nickel titanium alloy) and covered in a gold plated tungsten coil. The loop may be closed in some embodiments by a weld or solder joint 76.

Figure 6:
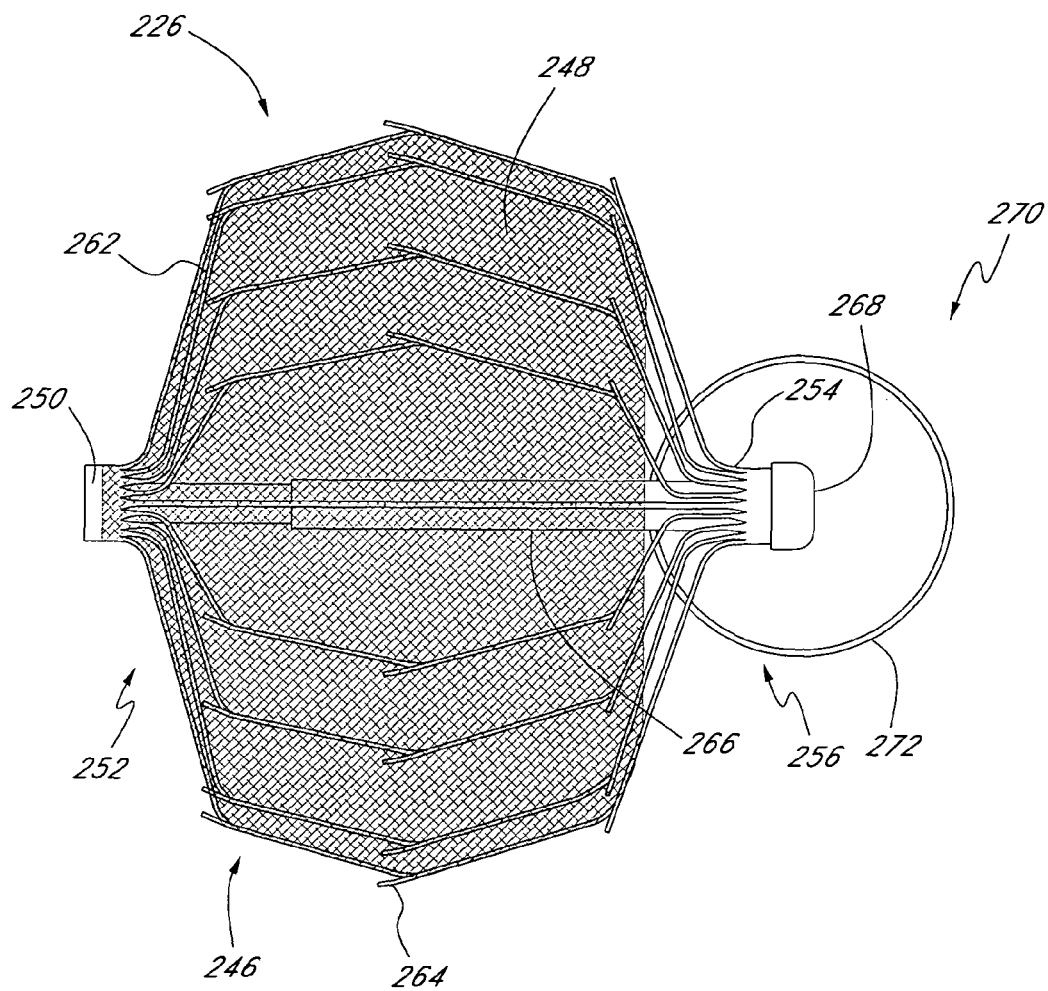
FIG. 6 is a plan view of a LAA implant with a retrievable portion in accordance with another embodiment.
Figure 7:
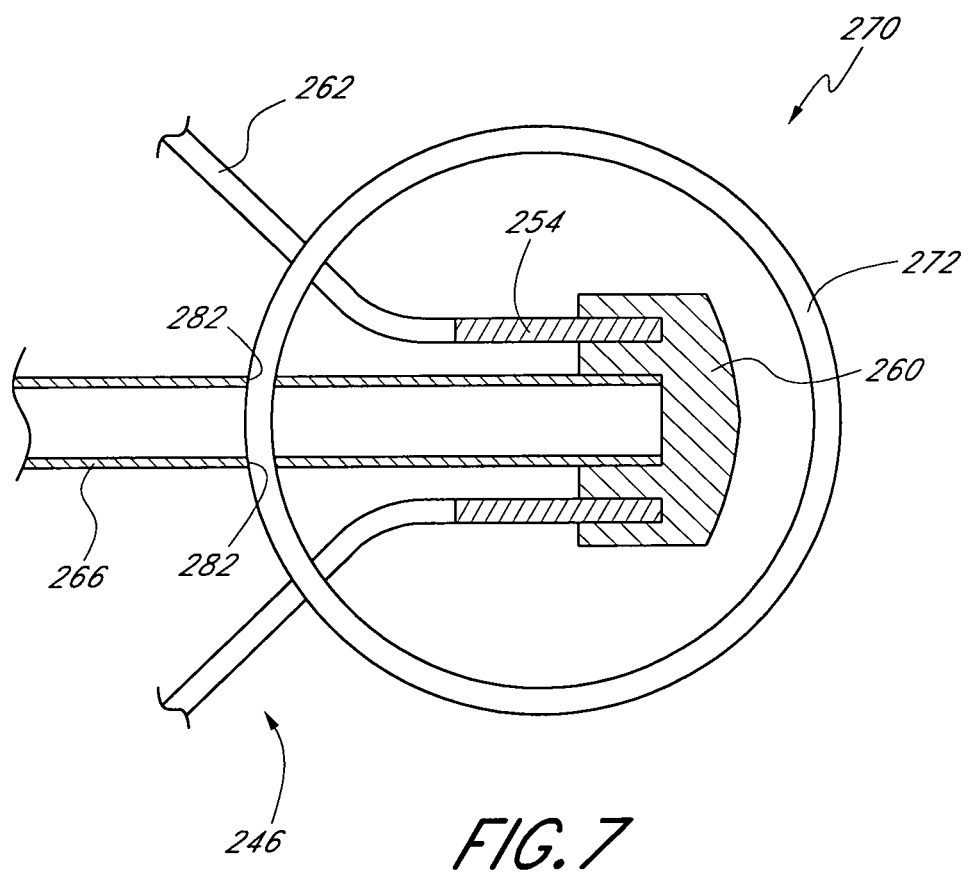
FIG. 7 is an enlarged partial cross-sectional view of the distal end of the implant with the retrievable portion of FIG. 6.

In accordance with another embodiment, shown in FIGS. 6 and 7, a retrieval portion 270 is connected to an implant 226. The retrieval portion 270 may comprise a loop 272 extending distally from implant 226. The distal guide tube 266 may comprise a pair of generally transverse passages 282. The loop 272 may pass between the supports 262 and through the passages 282 in the distal guide tube 266 to connect the loop 272 to the implant 226 and restrict translational movement of the loop 272 relative to the implant 226 in either a proximal or a distal direction. Interference between the loop 272 and the supports 262 inhibits rotational movement of the loop 272 relative to the supports 262 to maintain the spacing of the loop 272 from the implant 226.

Figure 8:
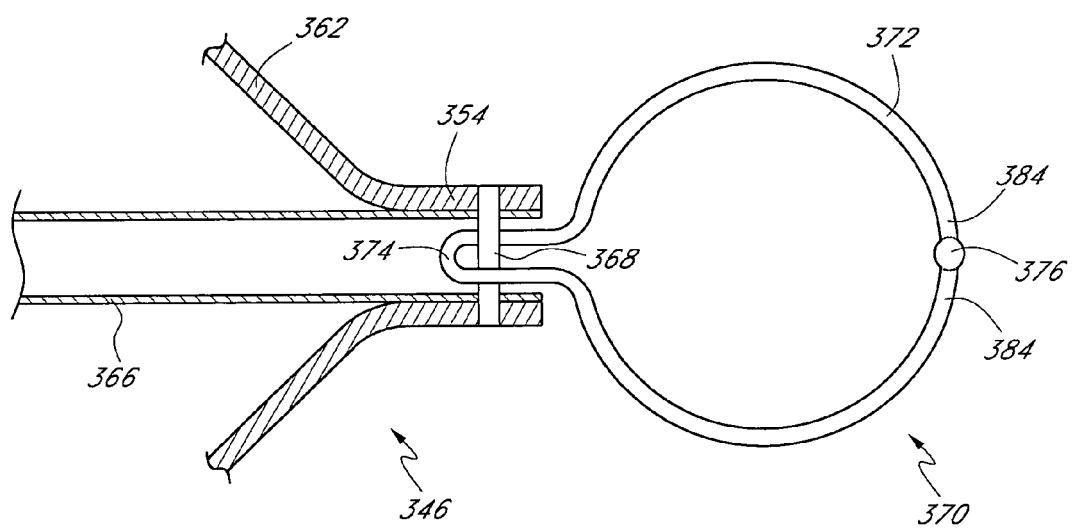
FIG. 8 is an enlarged partial cross-sectional view of the distal end of a LAA implant with a retrievable portion in accordance with another embodiment.

A retrieval portion 370 is connected an implant 326 in accordance with another embodiment, shown in FIG. 8. The retrieval portion 370 comprises a loop 372. The loop 372 has a segment 374 that extends into the distal guide tube 366 and around a crosspin 368. The ends 384 of the loop 372 may be joined at a joint 376 by welding, soldering, or other attachment joining method known to those of skill in the art.

In other embodiments, the retrieval portion may be attached to the frame by any other attachment technique known to those of skill in the art, such as by an adhesive, mechanical lock, pin, threads, clip, weld, solder, laser bond or weld, or friction coupling. In some embodiments, the ends 384 of the loop 372 may be located at a proximal end of the loop and welded, soldered, or otherwise attached directly to a distal end of the implant by any method known to those of skill in the art. In some embodiments, the retrieval portion may be integrally formed with the frame. For example, the retrieval portion can be formed from the material of the frame by laser cutting a tube.

Figure 9:
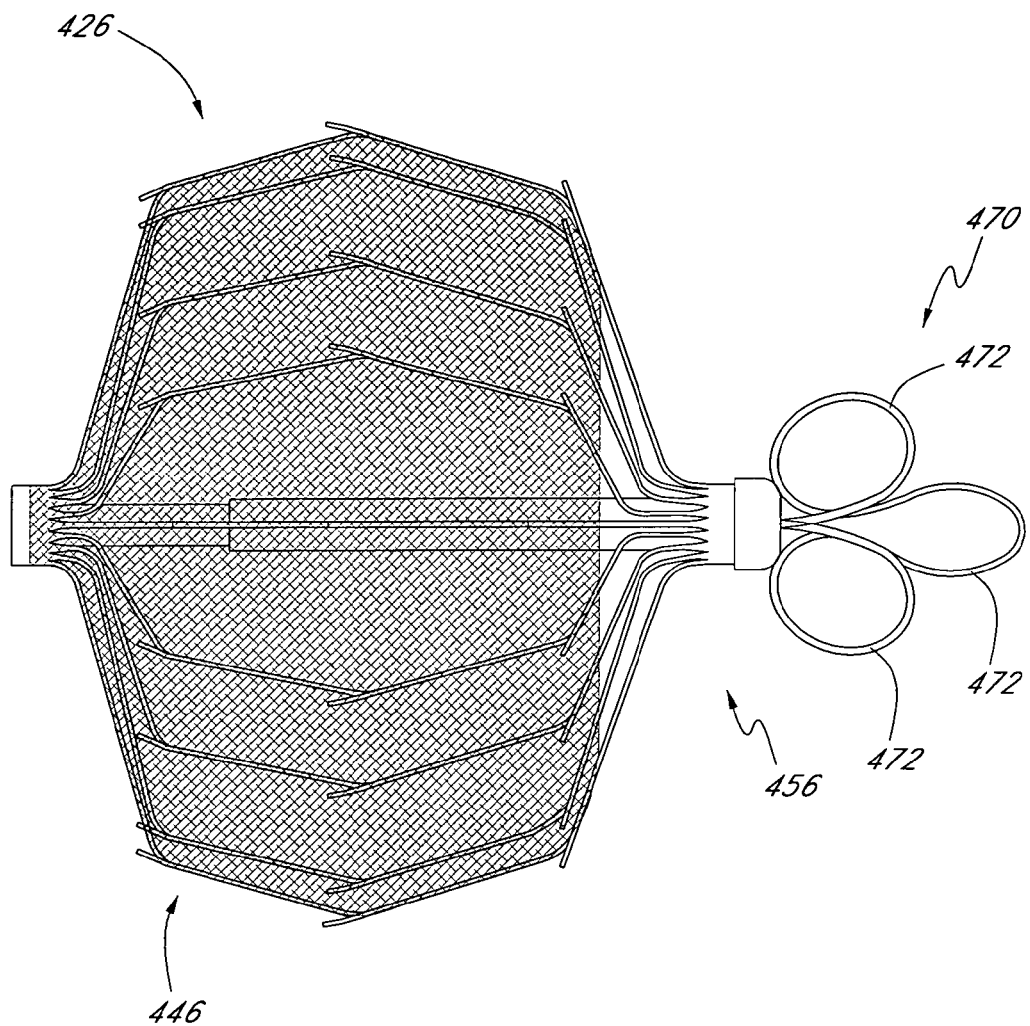
FIG. 9 is a plan view of a LAA implant with a retrievable portion in accordance with another embodiment.

In one embodiment, shown in FIG. 9, a retrieval portion 470 may comprise a plurality of loops 472 attached to the distal end 456 of implant 426. For example, 2, 3, 4, 5, or more loops may be provided.

An embodiment of a retrieval portion comprising a retrieval loop has been prototyped and animal tested. The prototyped device did not affect implantation ability. The ability to retrieve an embolized implant was tested in a narrow animal aortic overflow tract, which prevented embolization beyond the aortic valve. Bench testing in glass aortic bifurcation model showed quick and effective snaring and retrieval of the implantable device utilizing the loop and two snares of a retrieval catheter.

A method for retrieving an implant having a retrievable portion is illustrated in FIGS. 10-14. As described above, in the unlikely event that embolization of the implantable device occurs, the implantable device, substantially as described above, may be present in the left atrium, left ventricle, aorta, or other location. In one embodiment, illustrated in FIG. 10, an implant 526 with a retrieval portion 570 may be present in the aorta 540. The retrieval portion 570 may comprise a loop 572.

Figure 10:
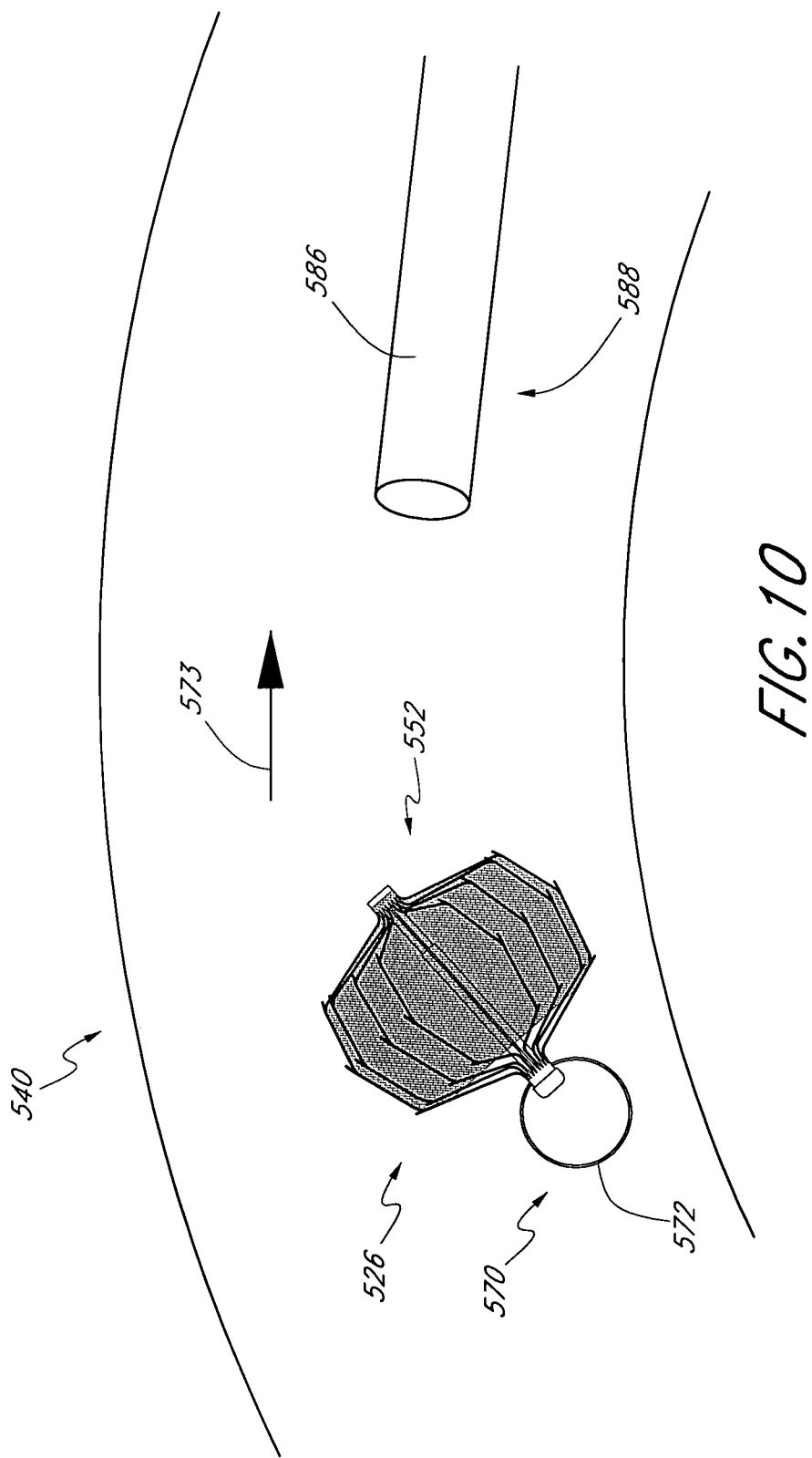
FIG. 10 is a schematic view of a patient's aorta with a sheath disposed near an embolized implant.

The implant 526 may have become oriented such that the proximal end 552 is located downstream from the distal end 556, as indicated by the arrow 573 in FIG. 10. The method as follows may be performed under fluoroscopy or any other visualization technique. A sheath 586 is introduced through the vasculature and is positioned near the implant 526, as shown in FIG. 10. In one embodiment, the sheath 586 may be introduced through the femoral artery. In other embodiments, particularly when the implant is located in the left ventricle, the sheath may be introduced through the femoral vein, advanced through the right atrium, inserted through the intraatrial septum, and directed to the left ventricle. In other embodiments, the sheath 586 may be introduced through the iliac artery, brachial artery, popliteal artery, radial artery, or other percutaneous access sites.

Figure 11:
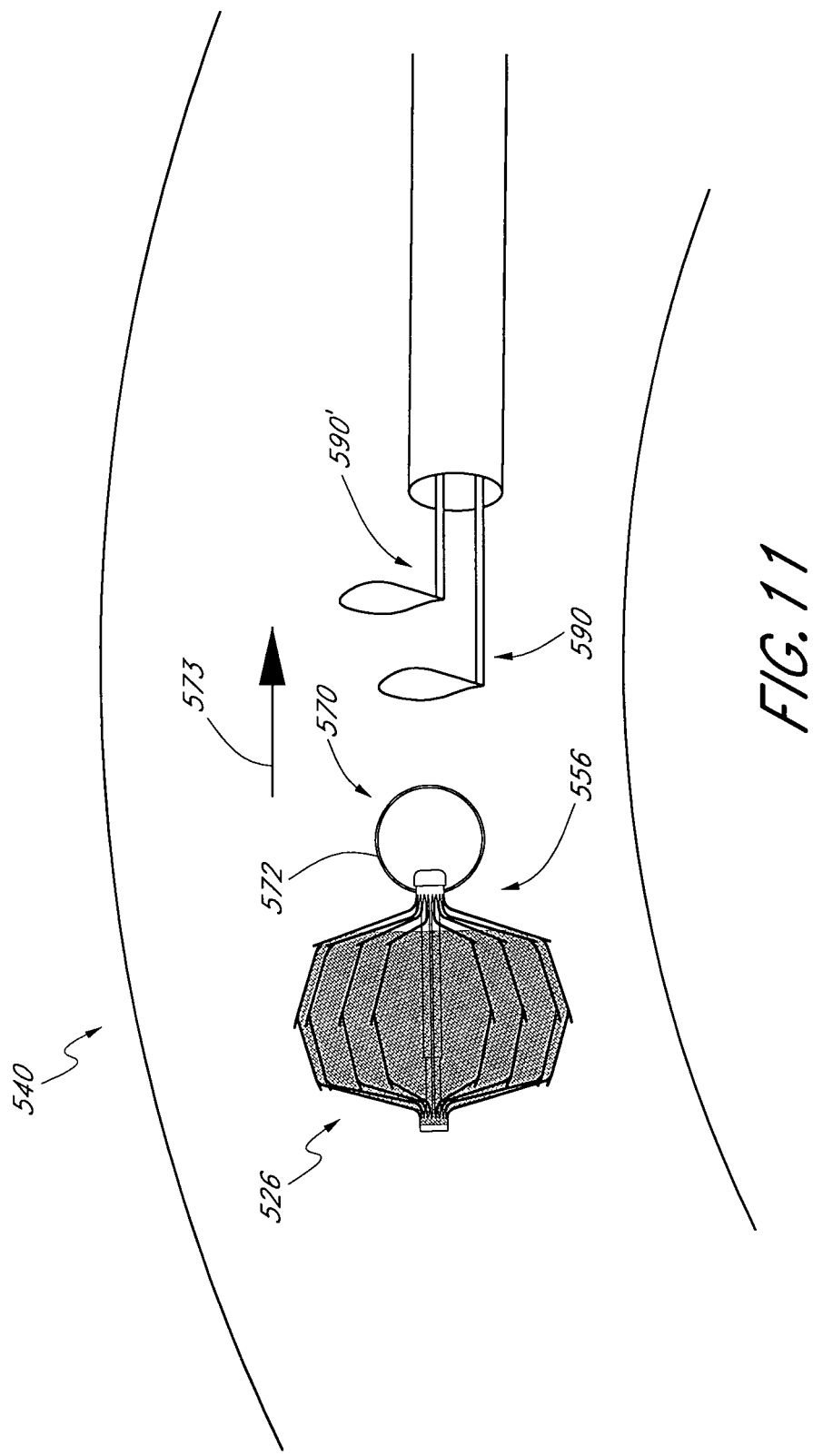
FIG. 11 is a schematic view as in FIG. 10, showing the implant oriented with the distal end facing downstream and retrieval devices extending out of the transeptal sheath.

The sheath 586 preferably has a linear or non-curved distal end 588. In some embodiments, the sheath 586 may be a transseptal sheath, such as transseptal sheath 12 described above. In one embodiment, the sheath has an inner diameter of 12 French. In other embodiments, the sheath may have an inner diameter ranging from about 9 French or less to about 25 French or more. Referring to FIG. 11, one or more retrieval devices 590 are delivered through the sheath 586. The retrieval device 590 may be a snare, grasper, hook, loop, or biopsy catheter or any device capable of grasping the retrieval portion 590. In one embodiment, the retrieval device 590 may be Amplatz GOOSE NECK® Snare produced by ev3 Inc. The retrieval device 590 may be used to manipulate the implant 526 within the aorta 540 such that the end 556 coupled to the retrieval portion 570 is next to the retrieval devices 590 and the sheath 586, as shown in FIG. 11. In one embodiment, percutaneous access is accomplished on the side contralateral to retrieval device access and a snare catheter is introduced to the vicinity of the implant and used to stabilize the implant while a retrieval device 590 is appropriately positioned. In one embodiment, the distal end 556 preferably is then facing downstream.

Figure 12:
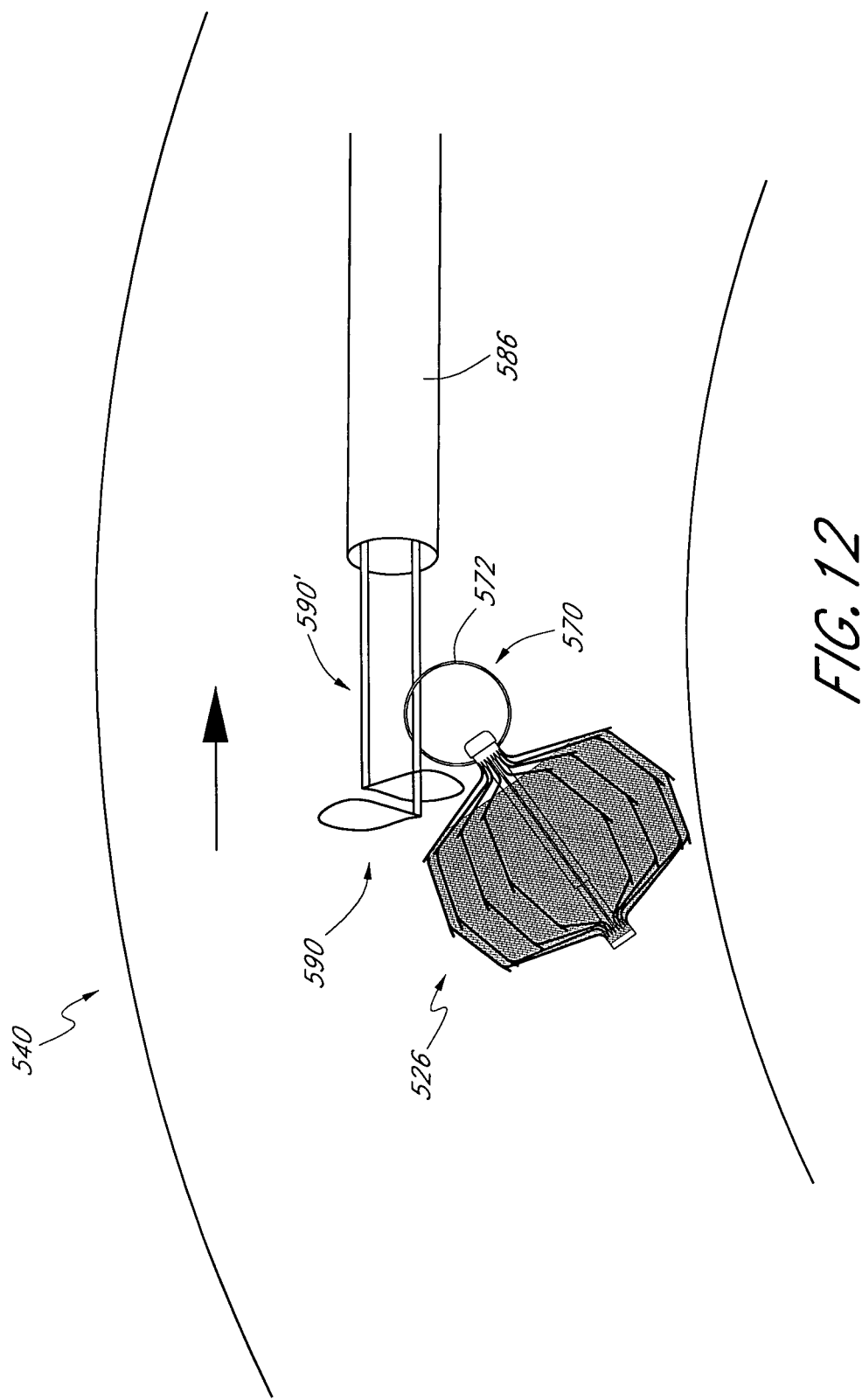
FIG. 12 is a schematic view as in FIG. 11, showing the first retrieval device passing through a retrieval portion and the second retrieval device.
Figure 13:
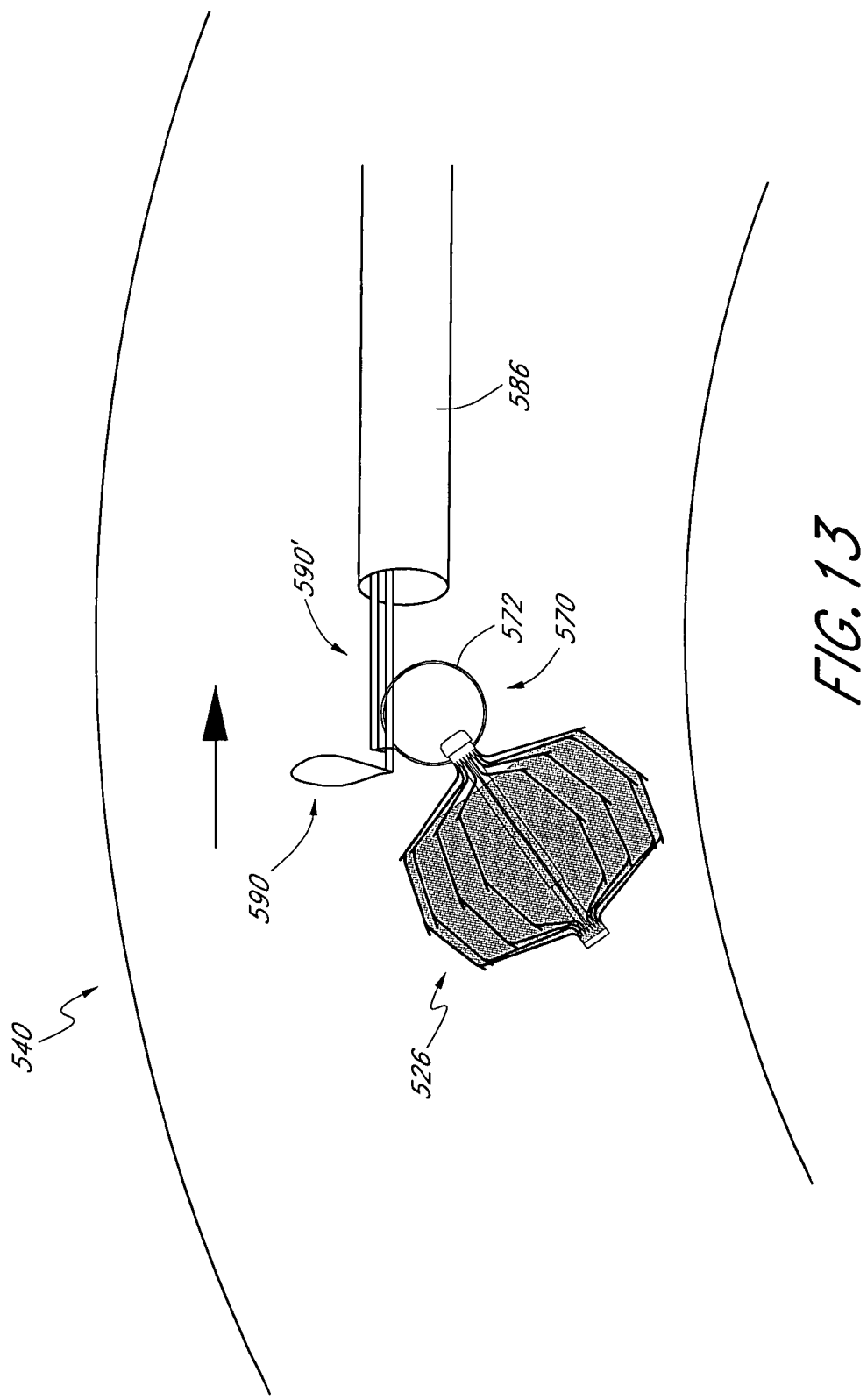
FIG. 13 is a schematic view as in FIG. 12, showing the second retrieval device tightened around the first retrieval device.
Figure 14:
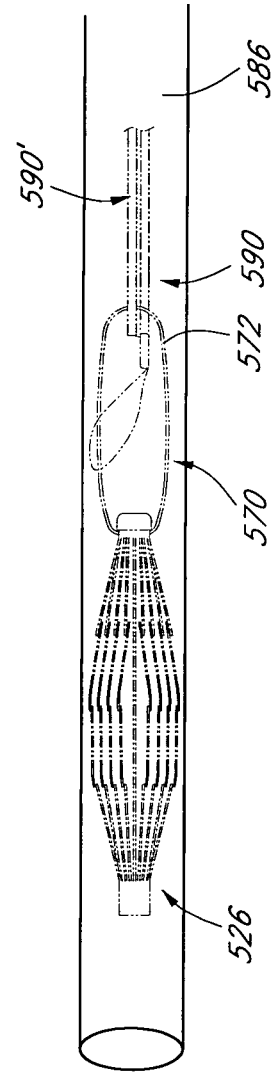
FIG. 14 is a schematic view as in FIG. 13, showing the retrieval devices proximally retracting the implantable device into the transeptal sheath.

The one or more retrieval devices 590 may be coupled to the retrieval portion 570 of the implantable device 526. Referring to FIG. 12, in one embodiment a first retrieval device 590 may be placed through the loop 572. A second retrieval device 590' may be placed over the first retrieval device 590. The second retrieval device 590' may be tightened onto the first retrieval device 590, as shown in FIG. 13. The first retrieval device 590 and second retrieval device 590' may be retracted proximally into the sheath 586 pulling the implant 526 into the sheath 586 by the loop 572, as illustrated in FIG. 14. The implant 526 preferably collapses as it is drawn into the sheath 586. It should be observed that the anchors 564 on implant 526 preferably face away from sheath 586 such that as the implant 526 is retracted proximally the anchors 564 do not snag, catch, tear, or rip the sheath 586 or the wall of the aorta 540.

Figure 15:
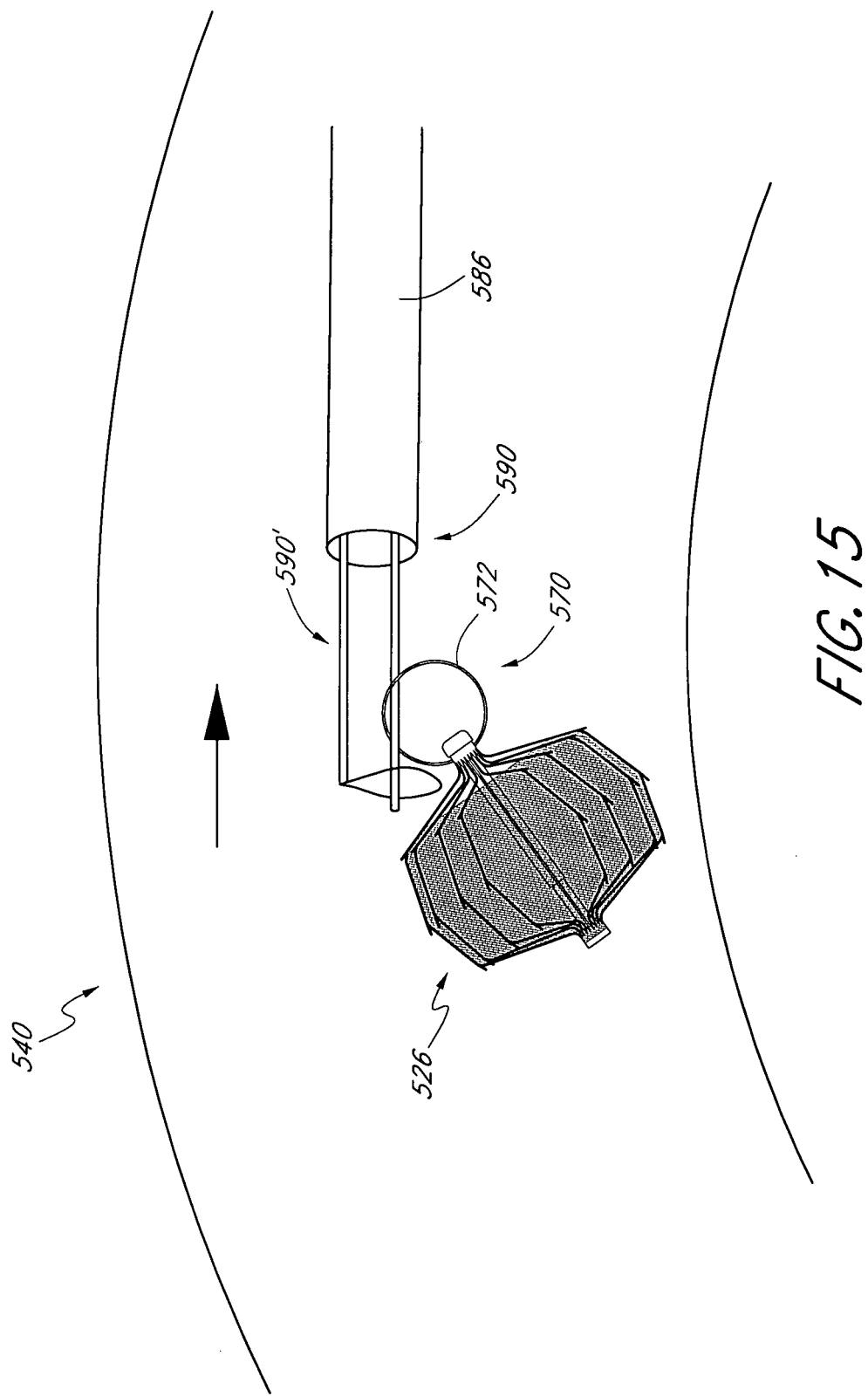
FIG. 15 is a schematic view showing a first retrieval device passing through a retrieval portion and a second retrieval device, in accordance with another embodiment.
Figure 16:
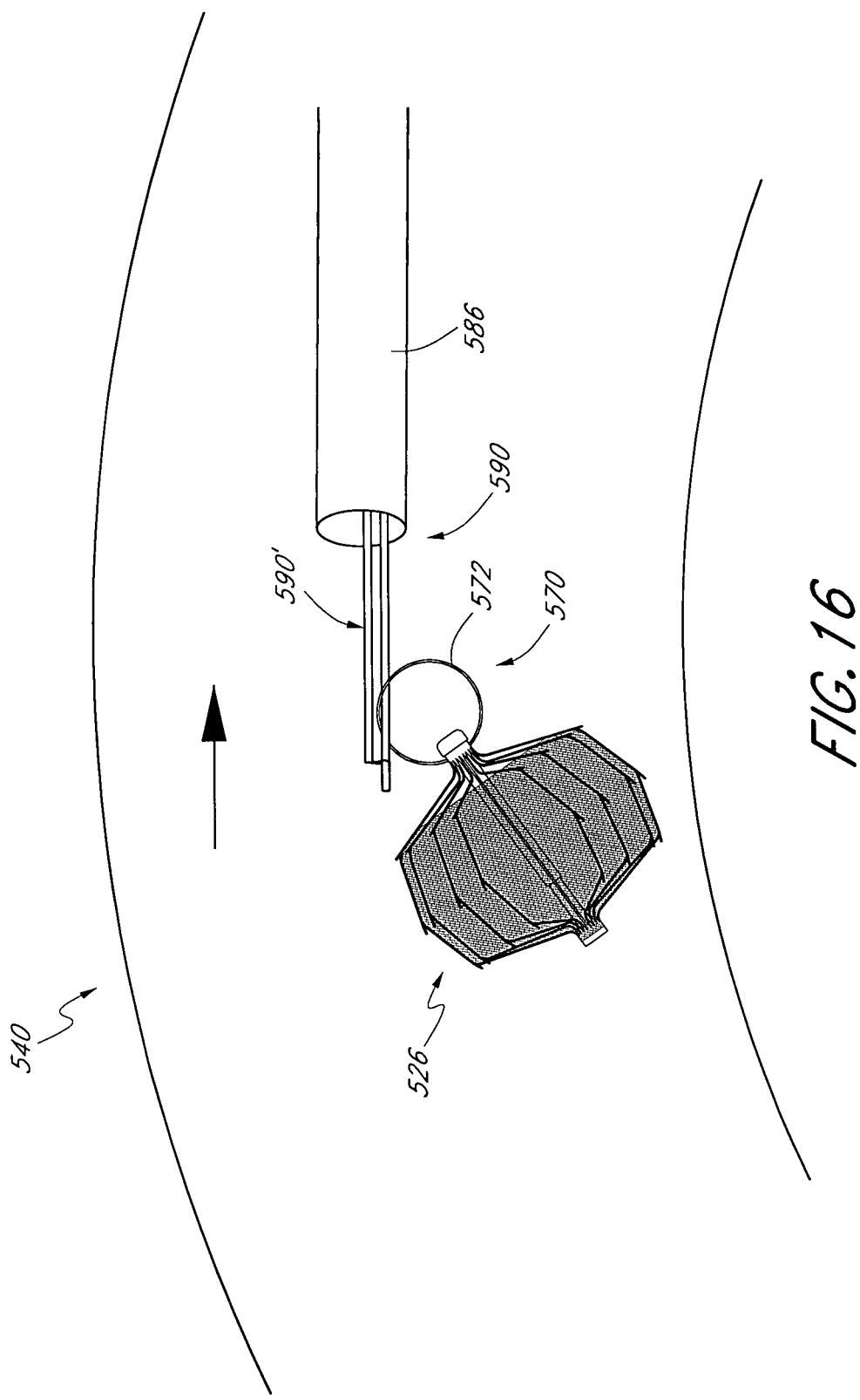
FIG. 16 is a schematic view as in FIG. 17, showing the second retrieval device tightened around the first retrieval device.

In one embodiment, a first retrieval device 590 may be a stiff wire or small bore catheter, as illustrated in FIGS. 15 and 16. The first retrieval device 590 comprising a stiff wire or small bore catheter may be placed through the loop 572. A second retrieval device 590' comprising a snare may be placed over the first retrieval device 590 comprising a stiff wire or small bore catheter. The snare 590' may be tightened onto the stiff wire or small bore catheter 590, as shown in FIG. 16. The retrieval devices 590 and 590' may be retracted proximally to pull the implant 526 into the sheath 586.

In another embodiment, the retrieval device may comprise a biopsy catheter. The biopsy catheter may be used to grasp the retrievable portion. The biopsy catheter may be retracted proximally into the sheath once the biopsy catheter has grasped the retrievable portion.

Figure 17:
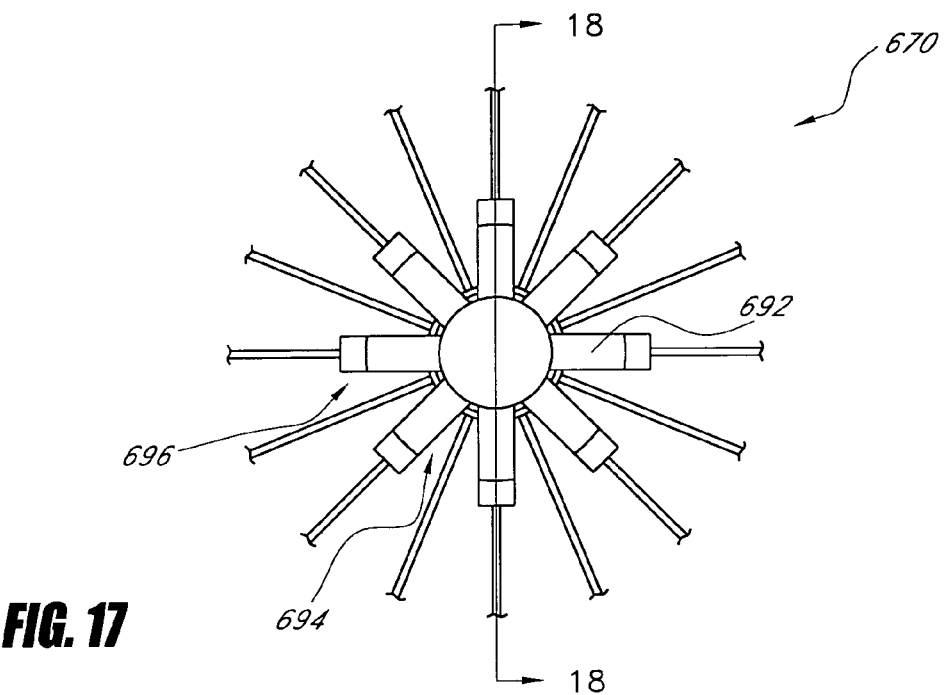
FIG. 17 is an end view of a LAA implant with a retrievable portion in accordance with one embodiment.
Figure 18:
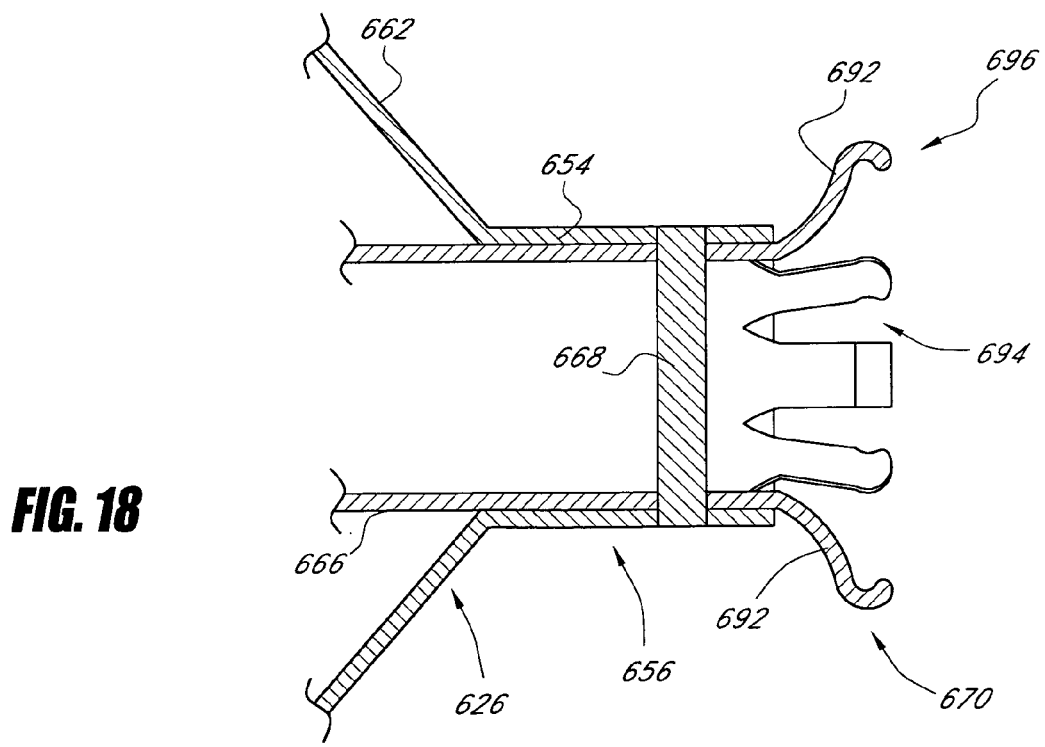
FIG. 18 is an enlarged partial cross-sectional view of the implant and retrievable portion of FIG. 17.

In one embodiment, shown in FIGS. 17 and 18, a retrievable portion 670 may comprise a plurality of extensions 692, each extending between a first end 694 and a second end 696. The retrieval portion 670 may comprise 2 to 16 or more extensions 692. In one embodiment, the retrieval portion 670 may comprise 8 extensions 692. The first ends 694 of extensions 692 may be attached to an implant 626. In one embodiment, the first ends 694 may be attached to a distal guide tube 666. The extensions 692 and the distal guide tube 666 may be integrally formed, as shown in FIG. 18. For example, distal guide tube 666 and extensions 692 may be made from tube stock by known laser cutting techniques. The extensions 692 may be attached to the distal guide tube 666 by any attachment technique known to those of skill in the art, such as by an adhesive, mechanical lock, pin, threads, clip, weld, solder, laser bond or weld, or friction coupling. In other embodiments, the extensions may be attached to the distal hub 654 or the supports 662 of implant 626. The distal guide tube 666 may be connected to the distal hub 654 by a pin 668.

The extensions 692 may extend distally from a distal end 656 of the implant 626, as illustrated in FIG. 18. The extensions 692 may distally extend about 0.5 mm or less to about 2 mm or more from the distal hub 654. In one embodiment, the extensions 692 may distally extend about 1.25 mm from the distal hub 654. The extensions 692 may be generally S-shaped and may extend radially outward. The extensions 692 may extend radially outward about 0.5 mm or less to about 2 mm or more from the distal hub 654. In one embodiment, the extensions 692 may extend radially outward about 1.25 mm from the distal hub 654. The second end 696 of the extensions 692 may point radially inward to prevent trauma to the anatomy should it be contacted by the extensions 692.

The extensions 692 may be comprised of metal, stainless steel, gold, plastic, NYLON, a combination of such materials, or any other material suitable for implantation within the body. In one embodiment, the extensions 692 may be made from a self-expanding material such as NITINOL with a hole drilled therein and a radiopaque gold rivet extending through the hole and enlarged outside both ends of the hole so as to fix the rivet to the extension. The extensions 692 may be resilient and may be compressed radially inwardly for insertion or retraction through a sheath.

Figure 19:
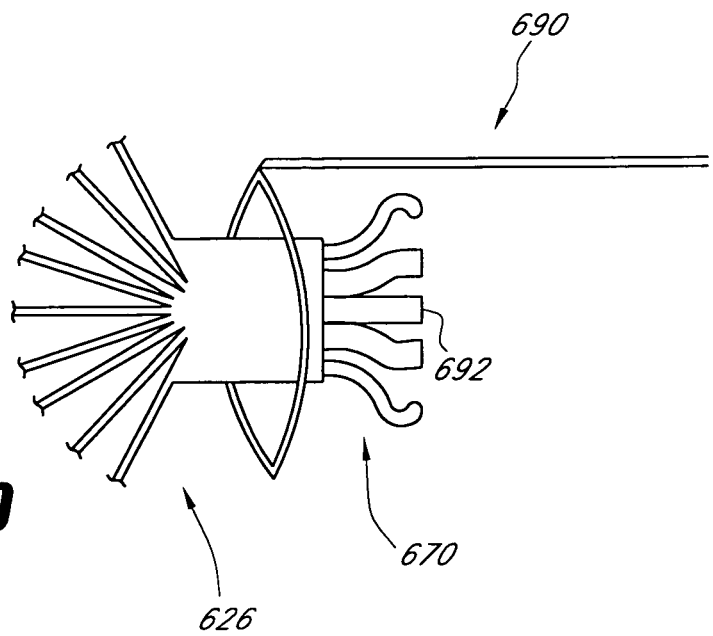
FIG. 19 is a schematic view of an implant with a retrieval portion in accordance with FIGS. 17 and 18 with a retrieval device.
Figure 20:
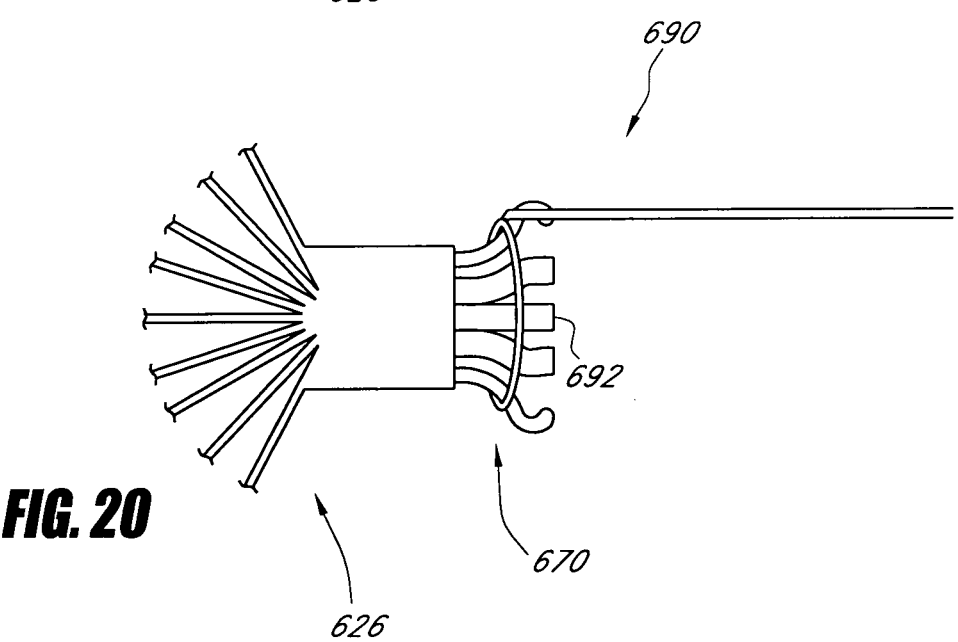
FIG. 20 is a schematic view as in FIG. 19, showing the retrieval device tightened around the retrievable portion.

A method of coupling a retrieval device 690 to the retrieval portion 670 is illustrated schematically in FIGS. 19 and 20. The retrieval device 690, such as a snare or loop may be disposed around the retrieval portion 670, as shown in FIG. 19. The retrieval device 690 may then be tightened around the retrieval portion 670, as illustrated in FIG. 20. The retrieval device 690 may retract the implant 626 into a sheath by pulling the retrieval portion 670.

Figure 21:
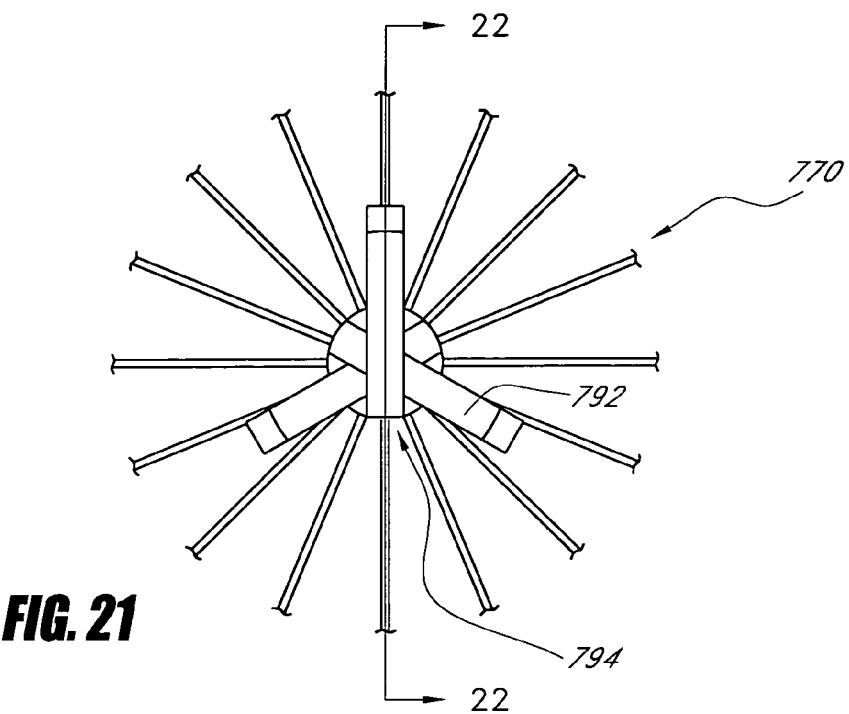
FIG. 21 is an end view of a LAA implant with a retrievable portion in accordance with another embodiment.
Figure 22:
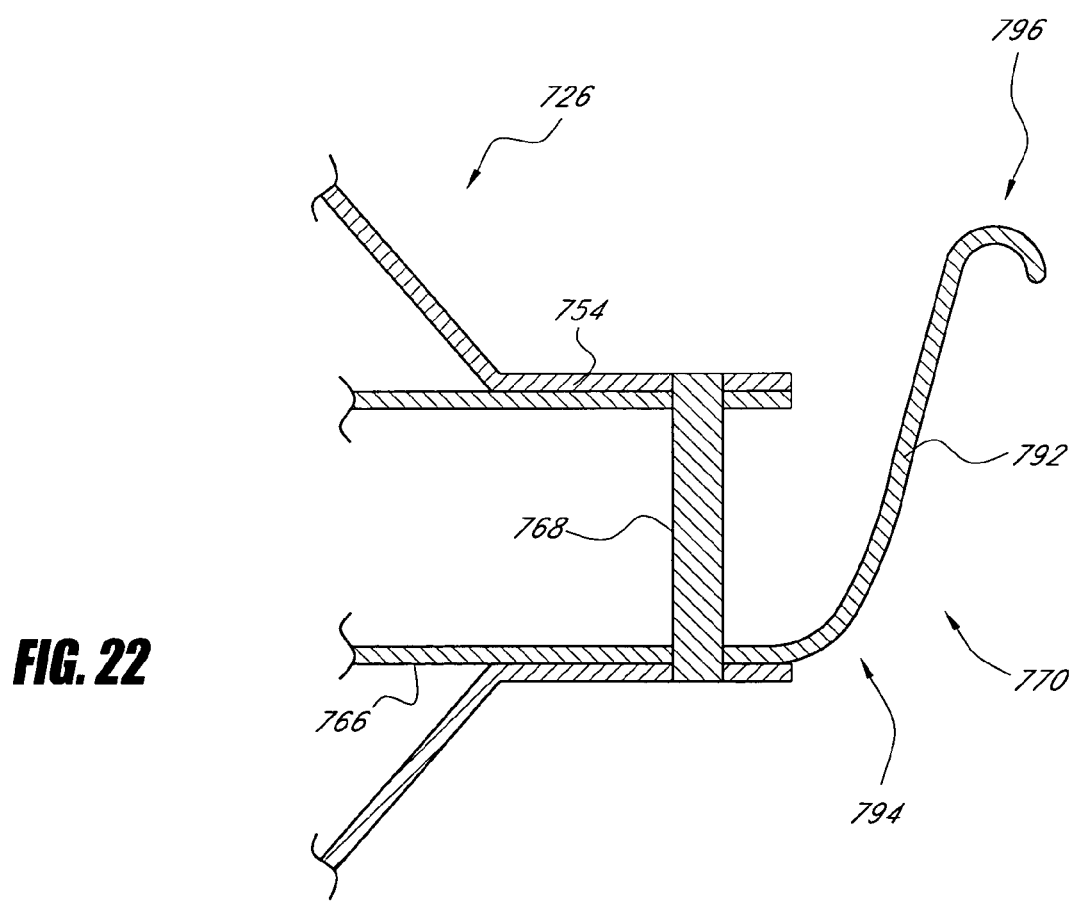
FIG. 22 is an enlarged partial cross-sectional view of the implant and retrievable portion of FIG. 21.
Figure 23:
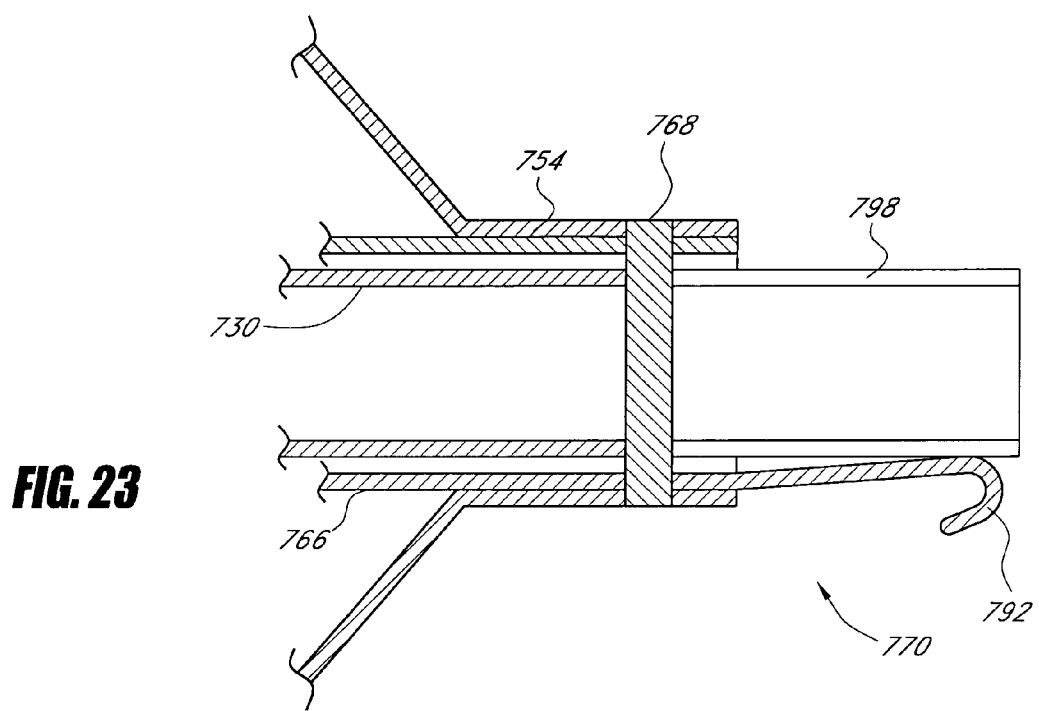
FIG. 23 is an enlarged partial cross-sectional view of the implant and retrievable portion of FIGS. 21 and 22.

In another embodiment, shown in FIGS. 21-23, a retrievable portion 770 may comprise a plurality of extensions 792 extending between first ends 794 and second ends 796. In one embodiment, the retrieval portion 770 may comprise 3 extensions 792. The first ends 794 of extensions 792 may be attached to an implant 726. In one embodiment, the first ends 794 may be attached to or integral with a distal guide tube 766. The distal guide tube 766 may be connected to the distal hub 754 by a pin 768.

The extensions 792 may extend distally from a distal end 756 of the implant 726, as illustrated in FIG. 22. The extensions 792 may distally extend about 0.5 mm or less to about 2 mm or more from the distal hub 754 in their natural state. In one embodiment, the extensions 792 may distally extend about 2 mm from the distal hub 754. The extensions 792 may be generally S-shaped and may extend transversely across the distal guide tube 766. The extensions 792 may extend transversely about 2 mm or less to about 6 mm or more. In one embodiment, the extensions 792 may extend transversely about 4 mm. The second end 796 of extensions 792 may point radially inward when deployed to prevent trauma to the anatomy near where the implant 726 is deployed.

The extensions 792 may be resilient and self-expanding and may be urged into a generally straight shape by an axially movable core 730 during placement of the implant 726 to permit the implant 726 with the retrievable portion 770 to be inserted through a sheath or catheter. The axially movable core 730 may include a slot 798 to allow the core 730 to extend past pin 768.

Figure 24:
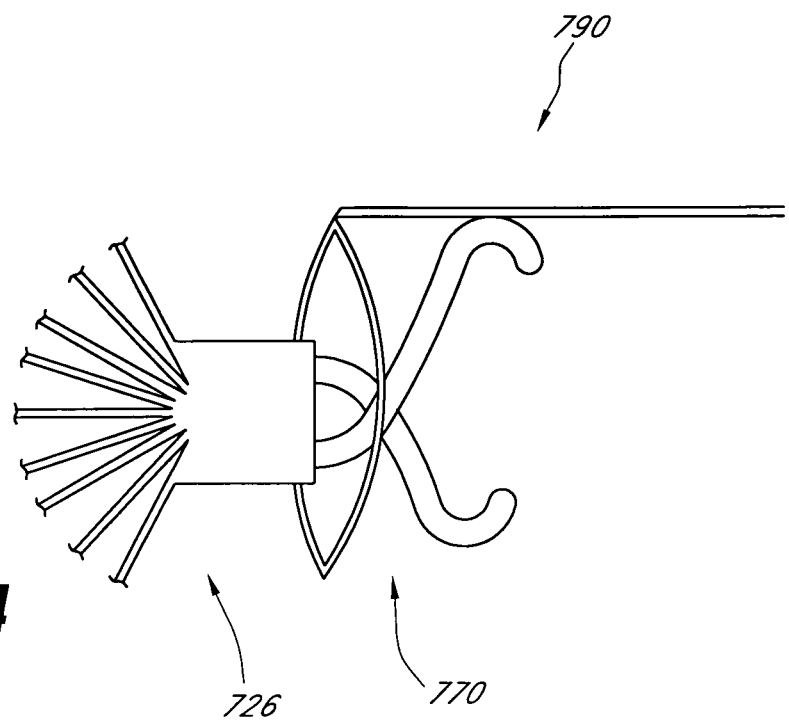
FIG. 24 is a schematic view of an implant with a retrieval portion in accordance with FIGS. 21-23 with a retrieval device.
Figure 25:
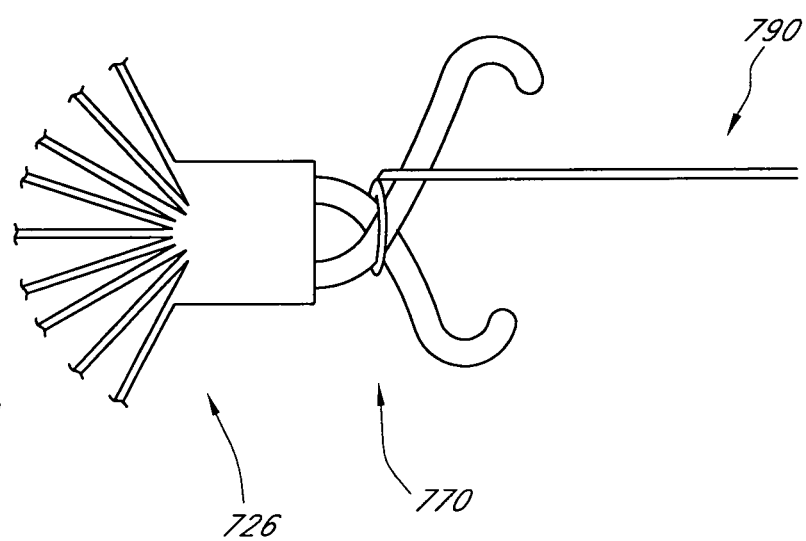
FIG. 25 is a schematic view as in FIG. 24, showing the retrieval device tightened around the retrievable portion.

A method of coupling a retrieval device 790 to the retrieval portion 770 is illustrated schematically in FIGS. 24 and 25. The retrieval device 790, such as a snare or loop may be disposed around the retrieval portion 770, as shown in FIG. 24. The retrieval device 790 may then be tightened around the retrieval portion 770, as illustrated in FIG. 20. The retrieval device 790 may retract the implant 726 into a sheath by pulling the retrieval portion 770.

Figure 26:
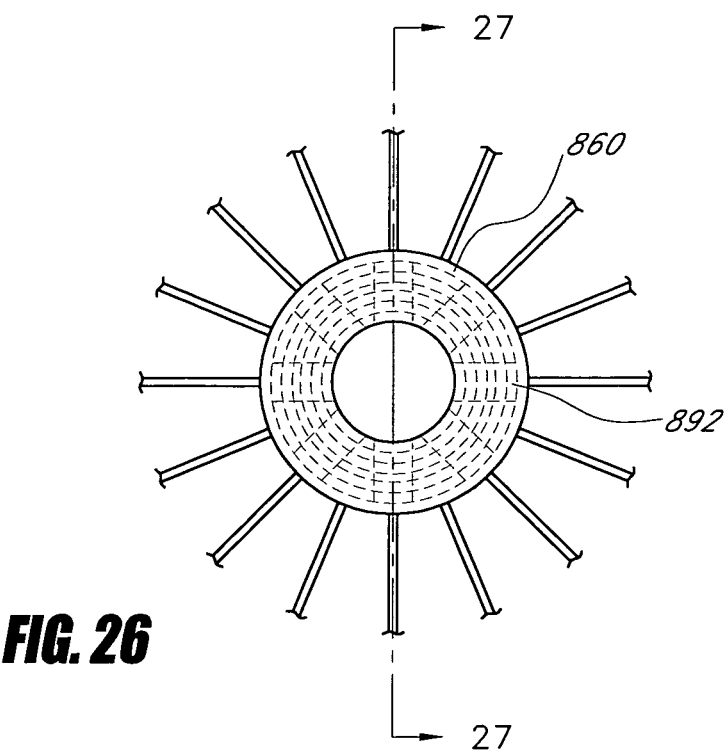
FIG. 26 is an end view of a LAA implant with a retrievable portion in accordance with another embodiment.
Figure 27:
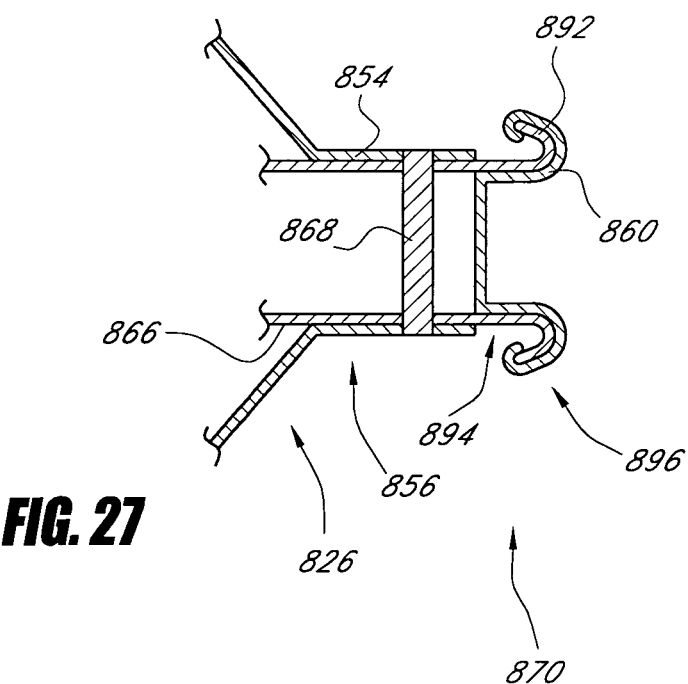
FIG. 27 is an enlarged partial cross-sectional view of the implant and retrievable portion of FIG. 26.

In another embodiment, shown in FIGS. 26-27, a retrievable portion 870 may comprise a plurality of extensions 892 extending between first ends 894 and second ends 896. In one embodiment, the retrieval portion 870 may comprise 8 extensions 892. The first ends 894 of extensions 892 may be attached to an implant 826. In one embodiment, the first ends 894 may be attached to a distal guide tube 866. The distal guide tube 866 may be connected to the distal hub 854 by a pin 868.

The extensions 892 may extend distally from a distal end 856 of the implant 826, as illustrated in FIG. 27. The extensions 892 may distally extend about 0.5 mm or less to about 4 mm or more from the distal hub 854. In one embodiment, the extensions 892 may distally extend about 2 mm from the distal hub 854. The extensions 892 may be generally J-shaped and may curve radially outward. The extensions 892 may be made from a self-expanding material, such as NITINOL. The extensions 892 may extend radially outward about 0.25 mm or less to about 2 mm or more. In one embodiment, the extensions 892 may extend radially outward about 0.5 mm. The second ends 896 of extensions 892 may comprise an atraumatic tip. The second ends 896 may be curved outwardly and proximally, and may be generally covered by a cap 860. The cap 860 may be made of polyethylene or other atraumatic material. In one embodiment, the cap 860 is composed of PEBAX.

Figure 28:
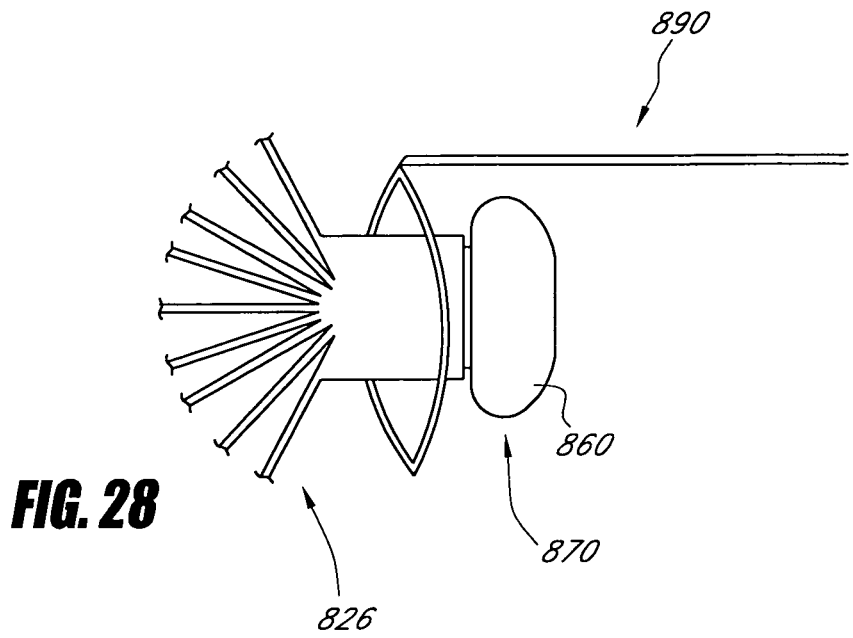
FIG. 28 is a schematic view of an implant with a retrieval portion in accordance with FIGS. 26 and 27 with a retrieval device.
Figure 29:
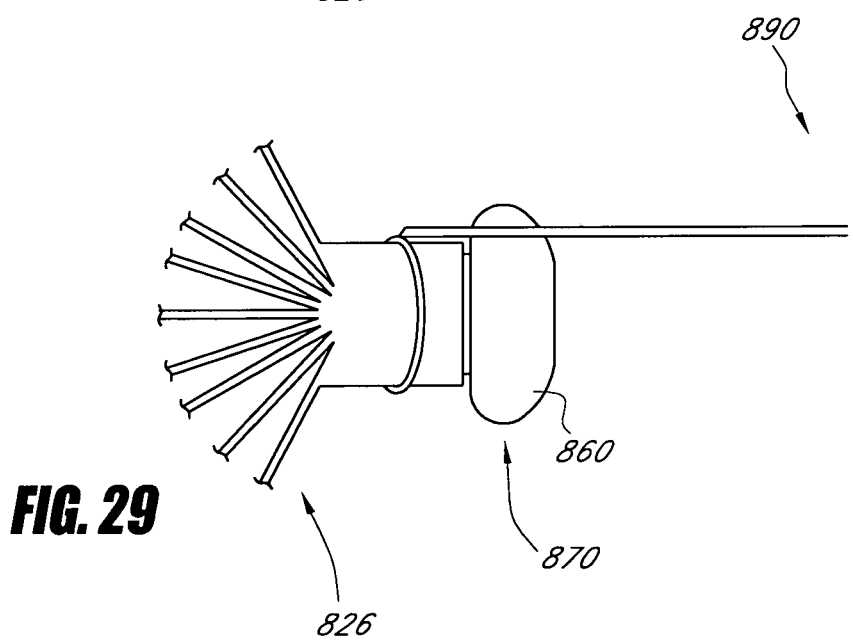
FIG. 29 is a schematic view as in FIG. 28, showing the retrieval device tightened around the retrievable portion.

A method of coupling a retrieval device 890 to the retrieval portion 870 is illustrated schematically in FIGS. 28 and 29. The retrieval device 890, such as a snare or loop may be disposed around the retrieval portion 870, as shown in FIG. 28. The retrieval device 890 may then be tightened around the retrieval portion 870, as illustrated in FIG. 29. The retrieval device 890 may retract the implant 826 into a sheath by pulling the retrieval portion 870.

Figure 30:
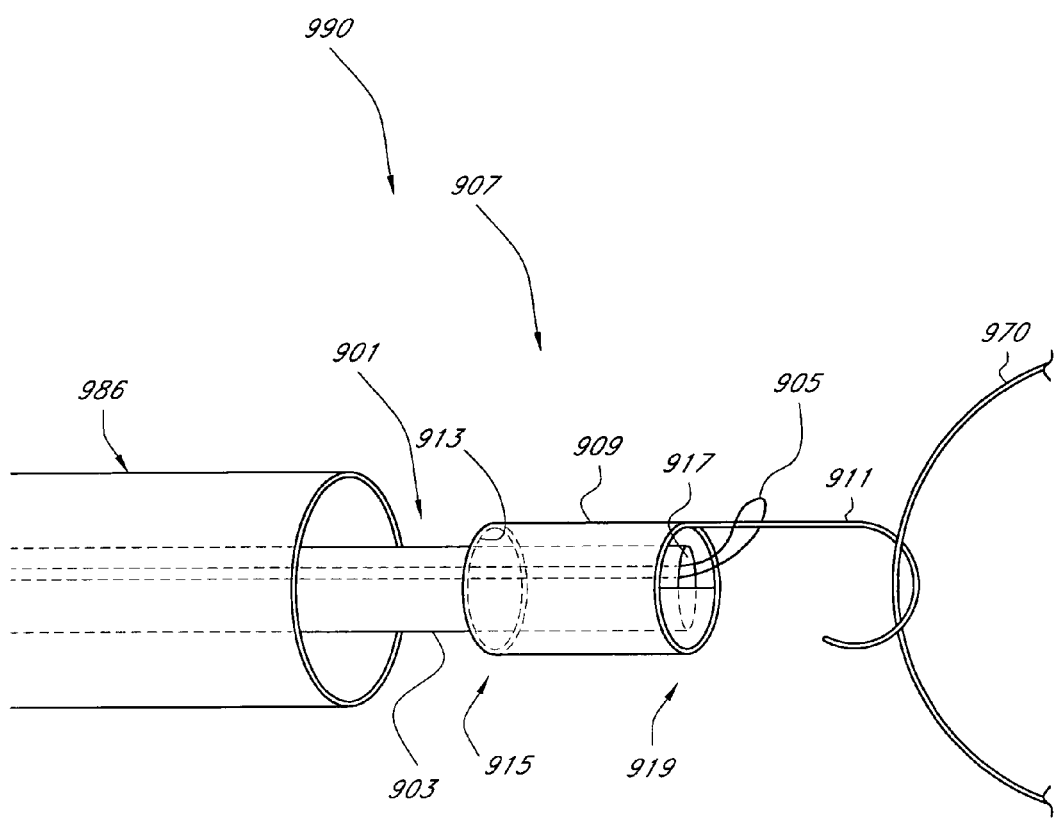
FIG. 30 is a schematic view of a retrieval device in accordance with one embodiment.

FIG. 30 illustrates a retrieval device 990 in accordance with one embodiment. The retrieval device 990 may be connected to a conventional snare 901. The snare 901 comprises a snare catheter 903 and a snare loop 905. The retrieval device 990 comprises an adapter 907. The adapter 907 may comprise a cylindrical body 909 and a hook 911. The cylindrical body 909 may have a proximal opening 913 at a proximal end 915 and a distal opening 917 at a distal end 919. The hook 911 may be attached to the distal end 919 of the cylindrical body 909.

The cylindrical body 909 and the hook 911 may be made from metal, such as NITINOL or stainless steel and tipped with radiopaque material. The cylindrical body 909 may be made of a different material than hook 911. In one embodiment, the cylindrical body 909 and the hook 911 may be made of NITINOL and be integrally formed. In other embodiments, the hook 911 may be attached to the cylindrical body 909 by any of a variety of metal bonding techniques such as a welding, brazing, interference fit such as threaded fit or snap fit, may be utilized. In one embodiment the hook 911 may be made of stainless steel and soldered to the body 909. In some embodiments, any of a variety of bonding techniques for dissimilar materials may be utilized, such as adhesives, and various molding techniques.

The adapter 907 may be connected to the snare 901 as illustrated in FIG. 30. The snare loop 905 may extend through the cylindrical body 909 and around the hook 911. The snare catheter 903 may be advanced distally relative to the snare loop 905 to tighten the snare 901 onto the adapter 907. In one embodiment, the proximal opening may be large enough to permit the snare catheter 903 to be disposed within the body 909, and the distal opening 917 of the body 909 may be smaller than the proximal opening 913 such that the snare catheter 903 is not permitted to pass beyond the distal opening 917. This restricts the movement of the adapter 907 relative to the snare 901 to facilitate manipulation, including pushing and pulling, by a clinician. Alternatively, the proximal opening 913 may be small enough not to permit the snare catheter from being disposed within the body 909.

The outer diameter of the cylindrical body 909 may range from about 5 French or less to about 12 French or more. In one embodiment, the outer diameter of body 909 is about 11 French. The hook may be wider or narrower than the body 909 but should be narrower than the luminal diameter of sheath 986. In one embodiment, the hook 911 is narrower than the body 909 so that the hook 911 is less likely to catch on a sheath or catheter when retracted therein.

The adapter 907 may be used in conjunction with the general method for retrieving an implantable device with a retrieval portion 970. The adapter 907 and snare 901 are preferably connected as described above before being inserted into the patient through the sheath. The adapter 907 may be coupled to the retrieval portion 970 by disposing the hook 911 around the retrieval portion 970. The adapter 907 may then be retracted proximally into the sheath 986 with the retrieval portion.

FIG. 31 illustrates a retrieval device 1090 in accordance with one embodiment. The retrieval device 1090 may be connected to a conventional snare 1001. The snare 1001 comprises a snare catheter 1003 and a snare loop 1005. The retrieval device 1090 comprises an adapter 1007. The adapter 1007 may comprise a tube 1021 extending between a proximal end 1023 and a distal end 1025, an articulation hole 1027, and snare attachment element 1029. The tube 1021 may also comprise a curved section 1037 near the distal end 1025.

The outer diameter of tube 1021 may range from about 4 French or less to about 6 French or more. In one embodiment, the outer diameter of the tube 1021 is about 5 French. The inner diameter of tube 1021 is preferably small enough to prevent the snare catheter 1003 from being advanced within the tube 1021 when the snare 1001 is tightened. The tube 1021 may be made of a resilient metal or plastic. In one embodiment, the tube 1021 may be made of NITINOL.

The articulation hole 1027 facilitates and controls folding of the tube 1021, as will be described below. The articulation hole 1027 may be range is size from about 0.5 French or less to about 3 French or more in diameter. In one embodiment, the articulation hole 1027 may be about 2 French in diameter. The articulation hole 1027 may be located from about 3 mm or less to about 5 mm or more from the distal end 1025 of the tube 1021 and is located on the inner bend surface of tube 1021 to facilitate tube folding. In one embodiment, the articulation hole 1027 may be located about 4 mm from the distal end 1025 of the tube 1021.

Figure 33:
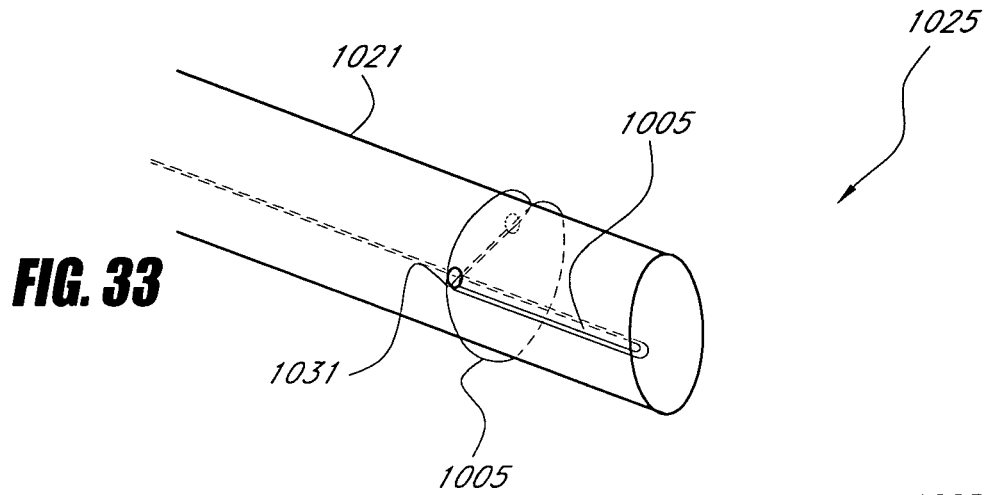
FIG. 33 is a schematic view of the distal end of a retrieval device in accordance with another embodiment.
Figure 34:
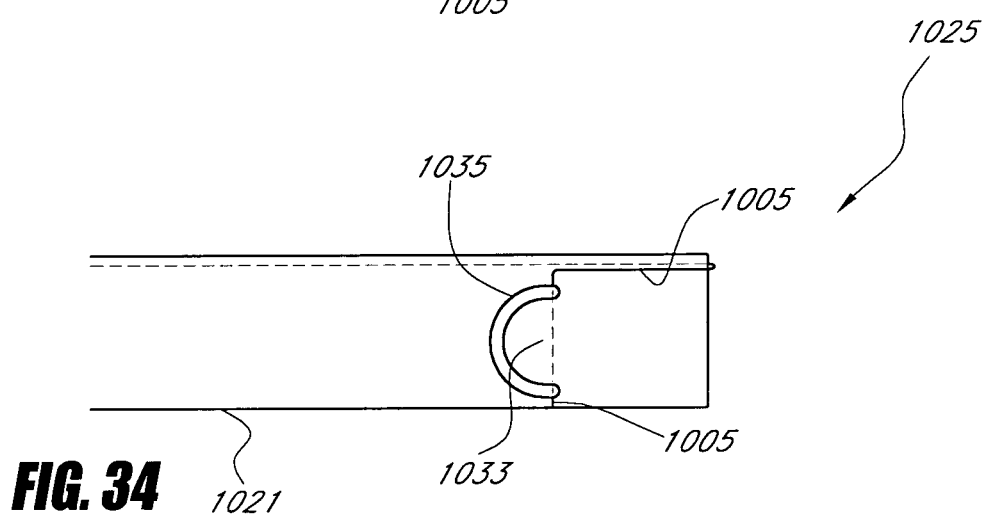
FIG. 34 is a top view of the distal end of a retrieval device in accordance with another embodiment.
Figure 35:
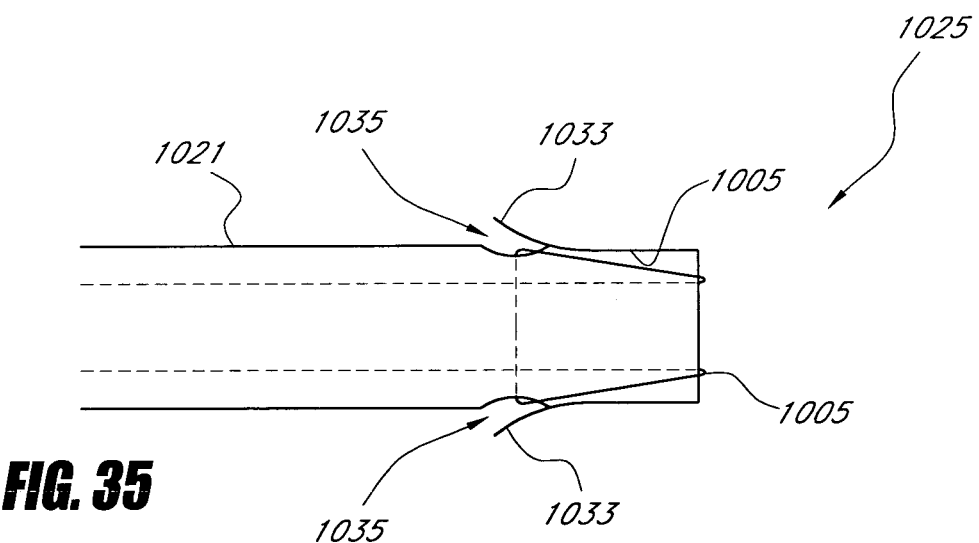
FIG. 35 is a side view of the distal end of the retrieval device of FIG. 34.

The snare attachment element 1029 allows the snare loop 1005 to be attached to the tube 1021. The snare attachment element 1029 may comprise a hole 1031 near the distal end 1025 of the tube 1021. The hole 1031 is preferably large enough to permit a snare loop 1005 to pass through it. The tube 1021 may be connected to the snare 1001 by passing the snare loop 1005 through the proximal end 1023 of the tube 1021, out the hole 1031, and around the distal end 1025 of the tube 1021, as illustrated in FIG. 31. In another embodiment, shown in FIG. 33, the tube 1021 may have two snare attachment holes 1031 near the distal end 1025. The snare loop 1005 may be extend out the distal end 1025 of the tube 1021, return along the exterior of the tube 1021, extend transversely across the tube 1021 through both of the holes 1031, and extend around the tube 1021. In yet another embodiment, illustrated in FIGS. 34 and 35, the snare attachment element 1029 may comprise a pair of generally diametrically opposed wings 1033 and slots 1035. Each wing 1033 may be made by laser cutting generally U- or C-shaped slot 1035 in the tube 2021 such that the distal end of the wing 1033 remains connected to the tube 1021. The wings 1033 may be flared generally radially outward to permit passage of the snare loop 1005 behind the wings 1033. The snare loop 1005 may be extend out the distal end 1025 of the tube 1021, return along the exterior of the tube 1021, and extend generally around the tube 1021 passing through the slots 1035.

The adapter 1007 may be used in conjunction with the general method for retrieving an implantable device with a retrieval portion 1070. The adapter 1007 may be coupled to the retrieval portion 1070 by disposing the distal end 1025 around or through the retrieval portion 1070 as dictated by the shape of the retrieval portion 1070. The snare 1001 may be tightened. As the snare 1001 is tightened the snare loop 1005 pulls on the distal end 1025 of the tube 1021, causing the tube 1021 to bend, as shown in FIG. 32. The bending of the tube 1021 will tend to be localized near the articulation hole 1027. Furthermore, the articulation hole 1027 will help control tube 1021 bending as the snare 1001 is tightened. Once the adapter 1007 has folded over it may be retracted proximally into the sheath 1086 with the retrieval portion 1070, as illustrated in FIG. 32.

Of course, it is to be understood that not necessarily all objectives or advantages described may be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof.

Embodiments of the invention are used to treat other bodily openings, lumen and cavities, besides the left atrial appendage. For example, in some embodiments, implantable devices for treating any heart opening or defect, such as a patent foramen ovale (PFO), atrial septal defect (ASD), ventricular septal defect (VSD), patent ductus arteriosus (PDA), aneurysm and aortico-pulmonary window are retrievable according to any of the methods and devices described above.

In addition, while particular forms of the invention have been described, it will be apparent that various modifications can be made without departing from the spirit and scope of the invention. Accordingly, it is not intended that the invention be limited to the particular embodiments described herein.

What is claimed is:

1. The method for removing an embolized implant from a patient, wherein the embolized implant is of the type having a dedicated retrieval loop forming a retrieval portion located apart from implant sealing surface, released from the left atrial appendage, comprising:
   positioning a sheath near the embolized implant;
   inserting a retrieval device of the type having a snare through the sheath;
   coupling the retrieval device snare to said retrieval loop portion of the embolized implant, the retrieval loop portion extending from the distal end of the implant; and
   retracting the embolized implant into the sheath.

2. The method of claim 1, wherein the embolized implant is located in the aorta.

3. The method of claim 1, further comprising positioning the sheath at the left atrial appendage prior to the implant becoming embolized.

4. The method of claim 1, wherein the implant comprises a plurality of anchors extending toward a proximal end of the implant, the anchors extending away from a distal end of the sheath when the implant is retracted into the sheath.

\* \* \* \* \*